US010321860B2

(12) United States Patent
Newberry

(10) Patent No.: US 10,321,860 B2
(45) Date of Patent: Jun. 18, 2019

(54) SYSTEM AND METHOD FOR GLUCOSE MONITORING

(71) Applicant: Sanmina Corporation, San Jose, CA (US)

(72) Inventor: Robert Steven Newberry, New Hope, AL (US)

(73) Assignee: Sanmina Corporation, San Jose, CA (US)

(*) Notice: Subject to any disclaimer, the term of this patent is extended or adjusted under 35 U.S.C. 154(b) by 743 days.

(21) Appl. No.: 14/866,500

(22) Filed: Sep. 25, 2015

(65) Prior Publication Data
US 2017/0014056 A1   Jan. 19, 2017

Related U.S. Application Data

(60) Provisional application No. 62/194,264, filed on Jul. 19, 2015.

(51) Int. Cl.
A61B 5/1455   (2006.01)
A61B 5/145    (2006.01)
(Continued)

(52) U.S. Cl.
CPC ........ A61B 5/14532 (2013.01); A61B 5/0022 (2013.01); A61B 5/1455 (2013.01);
(Continued)

(58) Field of Classification Search
None
See application file for complete search history.

(56) References Cited

U.S. PATENT DOCUMENTS 5,115,133 A   5/1992  Knudson
5,673,692 A   10/1997 Schulze et al.
(Continued)

FOREIGN PATENT DOCUMENTS

CN   102609627 A    7/2012
WO   WO2004047630   6/2004
(Continued)

OTHER PUBLICATIONS

Amir et al. Continuous noninvasive glucose monitoring technology based on 'Occlusion Spectroscopy'. J. Diabetes Science & Tech. vol. 1, No. 4 (Jul. 2007).
(Continued)

Primary Examiner — Eric F Winakur
Assistant Examiner — Marjan Fardanesh
(74) Attorney, Agent, or Firm — Loza & Loza, LLP; Julio M. Loza; Jessica W. Smith

(57) ABSTRACT

A glucose biosensor includes a plurality of optical fibers configured for placement within the ear canal. A first optical fiber emits light into the ear canal. A plurality of other optical fibers capture and transmit the reflected light back to the glucose biosensor. A plurality of photodetectors are configured in the glucose biosensor to detect the reflected light from the plurality of optical fibers. The glucose biosensor processes the detected light from each photodetector to determine a glucose level measurement. In an embodiment, the glucose biosensor also includes a wireless interface to transmit the glucose level measurements to a glucose meter and/or a gateway.

20 Claims, 28 Drawing Sheets

(51) Int. Cl.
*A61B 5/00* (2006.01)
*G06F 19/00* (2018.01)
*G16H 40/67* (2018.01)

(52) U.S. Cl.
CPC ............ *A61B 5/6817* (2013.01); *A61B 5/743* (2013.01); *G06F 19/00* (2013.01); *G16H 40/67* (2018.01); *A61B 5/6826* (2013.01); *A61B 2560/0223* (2013.01)

(56) References Cited

U.S. PATENT DOCUMENTS

| | | | |
|---|---|---|---|
| 5,823,966 | A | 10/1998 | Buchert |
| 5,983,121 | A * | 11/1999 | Tsuchiya ............... G01N 21/49 356/432 |
| 6,694,180 | B1 | 2/2004 | Boesen |
| 6,985,763 | B2 | 1/2006 | Boas et al. |
| 8,676,284 | B2 | 3/2014 | He |
| 9,149,216 | B2 | 10/2015 | Elsen et al. |
| 2004/0078219 | A1 | 4/2004 | Kaylor et al. |
| 2004/0157341 | A1 * | 8/2004 | Reynolds ........... A61B 5/14532 356/39 |
| 2005/0209516 | A1 | 9/2005 | Fraden |
| 2006/0094942 | A1 * | 5/2006 | Winther ............. A61B 5/14558 600/319 |
| 2007/0203405 | A1 | 8/2007 | Shimomura |
| 2008/0146890 | A1 * | 6/2008 | LeBoeuf .............. A61B 5/0059 600/300 |
| 2008/0165017 | A1 | 7/2008 | Schwartz |
| 2008/0208019 | A1 | 8/2008 | Nitzan |
| 2010/0274101 | A1 | 10/2010 | Lin et al. |
| 2010/0331631 | A1 | 12/2010 | MacLaughlin |
| 2011/0137141 | A1 | 6/2011 | Razoumov et al. |
| 2012/0095302 | A1 | 4/2012 | Adhikari |
| 2013/0110311 | A1 | 5/2013 | Ver Steeg et al. |
| 2013/0310669 | A1 | 11/2013 | Nitzan |
| 2014/0112940 | A1 | 4/2014 | Lane |
| 2015/0094914 | A1 | 4/2015 | Abreu |
| 2015/0109617 | A1 | 4/2015 | Gilbert et al. |
| 2015/0150453 | A1 | 6/2015 | Abreu |
| 2015/0182172 | A1 | 7/2015 | Shelley et al. |
| 2015/0282747 | A1 | 10/2015 | Thiele |
| 2015/0366471 | A1 | 12/2015 | Leboeuf et al. |
| 2016/0018257 | A1 | 1/2016 | Mirov et al. |
| 2016/0058347 | A1 | 3/2016 | Reichgott et al. |
| 2016/0066863 | A1 | 3/2016 | Thaveeprungsriporn et al. |
| 2016/0100781 | A1 | 4/2016 | Bechtel et al. |

FOREIGN PATENT DOCUMENTS

| | | |
|---|---|---|
| WO | WO2008006150 | 1/2008 |
| WO | WO2010128852 | 11/2010 |
| WO | WO2013127564 | 9/2013 |

OTHER PUBLICATIONS

Mahesh KC et al. "Wearable wireless intelligent multi-parameter health monitoring watch." Texas Instruments India Educators' Conf. (2013).

Townsend, Dr. Neil. "Pulse oximetry." Medical Electronics, Dr. Neil Townsend, Michaelmas Term (2001).

International Search Report & Written Opinion for PCT/US16/041791 dated Sep. 16, 2016; 11 pages.

International Preliminary Report & Written Opinion for PCT/US16/041791 dated Apr. 28, 2017; 29 pages.

\* cited by examiner

SYSTEM AND METHOD FOR GLUCOSE MONITORING

CLAIM OF PRIORITY UNDER 35 U.S.C. § 119

The present application claims priority under 35 U.S.C. § 119 to U.S. Provisional Application No. 62/194,264 entitled, "System and Method for Glucose Monitoring," filed Jul. 19, 2015, and hereby expressly incorporated by reference herein.

FIELD

This application relates to systems and methods of non-invasive blood analytic monitoring, including a glucose biosensor that detects glucose levels using one or more techniques. More particularly, the glucose biosensor transmits light into an ear canal and processes the light reflected from the ear canal to determine blood analytics, such as a glucose level, and wirelessly transmits the blood analytics to a gateway or glucose meter or user device.

BACKGROUND

Various techniques are available for obtaining blood glucose levels in patients with diabetes. One technique requires a small blood sample from the patients, e.g. from a finger prick. The blood sample is placed on a chemically prepared test strip and inserted into a glucose meter that analyzes the test strip and provides a blood glucose level. Unfortunately, to monitor their blood glucose levels, diabetics may need to prick their fingers multiple times within a day. This monitoring process can be painful, inconvenient and creates possible exposure to infections. Additionally, measurements with these devices present an error of uncertainty range between 6-7% depending on sample quality, human error, calibration, humidity, and hygiene in the sample area.

Thus, there is a need for an accurate, non-invasive blood analytic and glucose monitoring method and device that eliminates the pain of drawing blood as well as eliminates a source of potential infection.

SUMMARY

According to a first aspect, a glucose biosensor includes a light source that emits a light pulse into an ear canal and a plurality of optical fibers that capture the light reflected from the ear canal. A processing circuit is configured to obtain a glucose level measurement based on the reflected light captured by the plurality of optical fibers and a wireless transceiver is configured to transmit the glucose level measurement. The glucose biosensor further includes a first photodetector to receive the reflected light captured by a first one of the plurality of optical fibers and generate a first detected light signal, and a second photodetector to receive the reflected light captured by a second one of the plurality of optical fibers and generate a second detected light signal. An analog to digital converter circuit generates a first digital signal from the first detected light signal and a second digital signal from the second detected light signal. The processing circuit is further configured to compare the glucose level measurement to a predetermined threshold. When the glucose level measurement exceeds the predetermined threshold, the processing circuit generates an alert and a request to perform an alternative glucose measurement method.

According to a second aspect, a gateway includes at least one transceiver that communicates with a first glucose biosensor and a communications network. A processing circuit receives biosensor data from the first glucose biosensor, wherein the biosensor data includes a glucose level measurement; determines the glucose level measurement exceeds one or more predetermined thresholds; and transmits an alert to a third party caregiver over the communications network. The processing circuit may also generate a request for a second glucose biosensor to determine a glucose level measurement. In an embodiment, the first glucose biosensor is an ear biosensor, and the second glucose biosensor is a glucose meter.

According to a third aspect, an analytic biosensor includes a plurality of light sources configured to emit light into an ear canal and a plurality of optical fibers for capturing the light reflected from the ear canal. A processing circuit obtains a glucose level measurement based on the reflected light captured by the plurality of optical fibers using at least one of a plurality of measurement techniques, and a wireless transceiver transmits the glucose level measurement. In an embodiment, the processing circuit obtains a first glucose level measurement based on the reflected light using a first one of a plurality of measurement techniques and obtains a second glucose level measurement based on the reflected light using a second one of the plurality of measurement techniques. The processing circuit compares the first glucose level measurement with the second glucose level measurement; determines the first glucose level measurement and the second glucose level measurement are within a predetermined threshold; and obtains a final glucose level measurement based on the first glucose level measurement and the second glucose level measurement. When the first glucose level measurement and the second glucose level measurement are not within a predetermined threshold, the processing circuit determines to repeat at least one of: the first one of a plurality of measurement techniques or the second one of the plurality of measurement techniques. The processing circuit may also obtain a calibration using the plurality of measurement techniques, wherein the plurality of measurement techniques may include: infrared absorption spectroscopy, Raman spectroscopy, thermal emission spectrometry, flourophoresence, and photoacoustic spectrometry.

DETAILED DESCRIPTION

Figure 1:
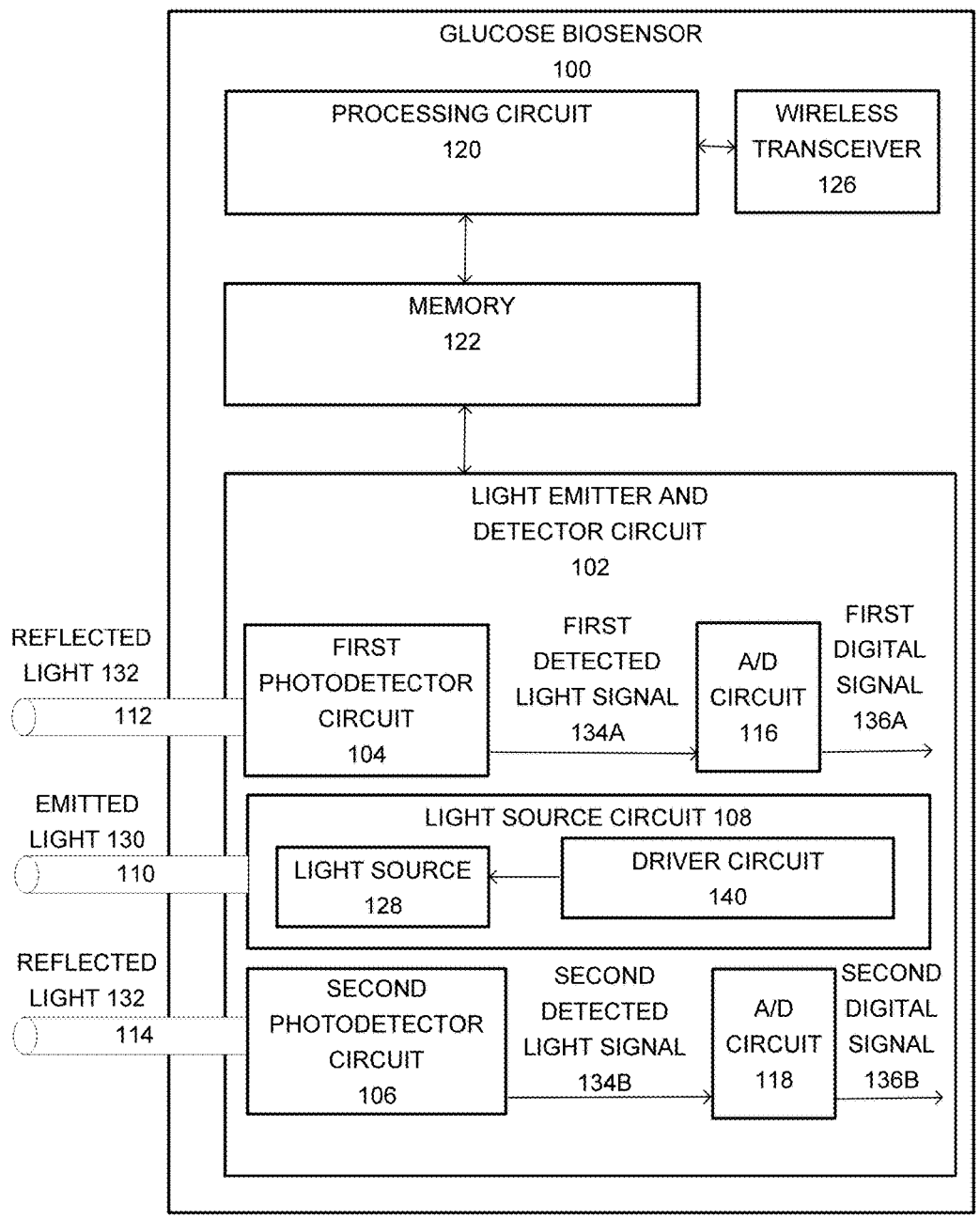
FIG. 1 illustrates a schematic drawing of an exemplary embodiment of a glucose biosensor.

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview

In first exemplary embodiments, a glucose biosensor includes optical fibers to emit ultraviolet (UV) light into an ear canal of a patient while one or more photodetectors in the glucose biosensor detect the reflected UV light. The glucose biosensor processes the reflected UV light from the ear canal to determine a glucose level measurement. In an embodiment, the glucose biosensor includes at least three optical fibers configured for placement within the ear canal. A first optical fiber emits UV light into the ear canal while the two other optical fibers capture and transmit the reflected UV light back to the glucose biosensor. Two photodetectors are configured in the glucose biosensor to detect the reflected light from the two optical fibers. The glucose biosensor processes the detected light from each photodetector to determine a glucose level measurement. In an embodiment, the glucose biosensor also includes a wireless interface to transmit the glucose level measurements to a glucose meter and/or a gateway. The gateway includes a communications interface for communicating over a wired or wireless network and may transmit the glucose level measurements to a hospital, doctor, or pharmacy or other third party caregiver. The gateway may also communicate the glucose level measurements to a central application server that includes a web-based user application for tracking and monitoring glucose level measurements and other biosensor data.

In second exemplary embodiments, an analytic biosensor is configured to perform monitoring of biometric analytical markers, including glucose levels, using a combination of two or more non-invasive techniques that analyze light reflected from an ear canal. For example, the techniques may include: near infrared spectroscopy, Raman spectroscopy, flourophoresence, thermal emissions, photoacoustic and polarimetry. In use, two or more of the techniques are employed to obtain biometric measurements. An average or mean of the biometric measurements from the two or more techniques is used for calibration of the analytic biosensor. The analytic biosensor is also configured to non-invasively measure other biometric data, such as pulse rate, blood pressure, peripheral oxygen (SpO2) saturation amounts, body temperature, various electrolytes and many common blood analytic levels, such as bilirubin amount.

Exemplary Embodiments of a Glucose Biosensor

FIG. 1 illustrates a schematic drawing of an exemplary embodiment of a glucose biosensor 100. The glucose biosensor 100 includes a processing circuit 120, a memory 122 and a wireless transceiver 126. For example, the memory 122 is a non-transitory, processor readable medium that stores instructions which when executed by the processing circuit 120, causes the processing circuit 120 to perform one or more functions described herein. The wireless transceiver 126 may operate in the 900 MHz range over a serial link using a proprietary protocol or may utilize a standard protocol in the 900 MHz range, such as IEEE 802.11ah, Zigbee, IEEE 802.15-11 etc. In other embodiments, the wireless transceiver 126 operates in one or more other wireless frequency bands or protocols, such as near field communication, short range radio frequency, RFID, infrared link, Bluetooth, or other short range wireless communication protocol.

The glucose biosensor 100 also includes a light emitter and detector circuit 102 having a first photodetector circuit 104, a second photodetector circuit 106 and a light source circuit 108. The light source circuit 108 includes one or more light sources 128, such as a light emitting diode (LED) or a laser circuit and a driver circuit 140 for controlling the one or more light sources 128. The first photodetector circuit 102 and the second photodetector circuit 106 each include, for example, a photodiode or other component operable to detect UV light and convert the detected UV light to an analog signal. The first photodetector circuit 104 is coupled to a first analog to digital A/D circuit 116, and the second photodetector circuit 106 is coupled to a second A/D circuit 118. In an embodiment, UV light is in a range from approximately 300 nm to 10 nm, including near UV light in a range from approximately 300-400 nm.

The light emitter and detector circuit 102 is optically coupled to a plurality of optical fibers 110, 112, 114. In an embodiment, the plurality of optical fibers 110, 112, 114 includes a first optical fiber 110 optically coupled to the light source circuit 108, a second optical fiber 112 optically coupled to the first photodetector circuit 104 and a third optical fiber 114 optically coupled to the second photodetector circuit 106. The plurality of optical fibers 110, 112, 114 are encased within an earpiece or ear bud or other casing that is configured to fit within an outer ear canal of a patient. In an embodiment, a first optical fiber 112 and a second optical fiber 114 are optically coupled to the first and second photodetector circuits 104 and 106, respectively. The first and second optical fibers 112, 114 are positioned around a third optical fiber 110 that is optically coupled to the light source circuit 108. As such, the optical fiber 110 optically coupled to the light source circuit 108 is configured to rest within the middle of the other two outer optical fibers 112 and 114. However, other configurations and numbers of the plurality of optical fibers 110, 112, 114 may also be implemented.

In use, the light source circuit 108 emits a series of pulses of light in one or more intervals, e.g. three pulses of light in each of at least three intervals. For example, in a first interval, such as a 10 ms interval, the light source circuit 108 emits at least three pulses of light. In a second interval, the light source circuit 108 emits three pulses again and three more pulses in a third interval. The light source circuit 108 then waits for a predetermined waiting period, such as 30-60 seconds, before emitting another series of pulses in one or more intervals. The waiting period between the series of pulses helps to prevent a rise in ear canal temperature that may affect the results. This process of emitting a series of pulses in one or more intervals and then waiting for a predetermined waiting period is continuously repeated or may be repeated at predetermined time periods, such as at 5 minute, 15 minute or longer time periods.

The emitted light 130 is transmitted into the outer ear canal by the middle optical fiber 110. The emitted light 130 is reflected back by membranes in the outer ear canal and/or the inner ear canal. The outer optical fibers 112 and 114 capture the reflected light 132 and transmit the reflected light 132 to the first and second photodetector circuits 104, 106, respectively. The first photodetector circuit 104 detects the reflected light 132 and generates a first detected light signal 134*a*. The first detected light signal 134*a* is transmitted to a first A/D circuit 116 configured to convert the first detected light signal 134*a* into a first digital signal 136*a*. Similarly, the second photodetector circuit 106 detects the reflected light 132 and generates a second detected light signal 134*b*. The second detected light signal 134*b* is transmitted to a second A/D circuit 118 that is configured to convert the second detected light signal 134*b* into a second digital signal 136*b*. The processing circuit 120 receives and processes the first and second digital signals 136*a*, 136*b* to determine a glucose level measurement.

In an embodiment, the light source circuit 108 emits light in the UV range, e.g. at approximately 430 nm. Blood based proteins associated with glucose levels in the blood stream reflect UV light at lower energy levels. Thus, the reflected UV light detected by the glucose biosensor 100 has a lower energy level than the emitted light. The decrease in the energy level of the reflected UV light provides an indicator of blood glucose levels. The glucose biosensor 100 in an embodiment determines a received power level of the reflected UV light from the first and second digital signals 136*a*, 136*b* and performs an integral summation of the received power levels to determine a glucose level measurement, as described in more detail herein.

In another embodiment, the glucose biosensor 100 performs a spectral analysis of the reflected UV light to determine a glucose level measurement. For example, the reflected UV light includes spectral information of the emitting body tissue. The spectral characteristics of the reflected UV light are analyzed by the glucose biosensor 100 to determine a glucose level measurement.

In another embodiment, a phase change of the reflected UV light is detected. The phase change of the reflected UV light between the first photodetector circuit 104 and the second photodetector circuit 106 can be translated into a glucose level measurement.

In another embodiment, the glucose biosensor 100 transmits infrared (IR) light into the ear canal rather than near UV light, and the first and second photodetector circuits 104, 106 are operable to detect the reflected IR light. For example, in an embodiment, the light source circuit 108 transmits IR light at approximately 940 nm. The glucose biosensor 100 processes the reflected IR light to determine glucose level measurements. In another embodiment, the light source circuit 108 is operable to transmit light in a plurality of spectrums. For example, one or more light sources 128 emit a combination of two or more of UV light, visible light and IR light. The first and second photodetector circuits 104, 106 are operable to detect the light in the plurality of spectrums. The glucose biosensor 100 processes the reflected light 132 in the plurality of spectrums to determine a glucose level measurement.

In another embodiment, the glucose biosensor 100 performs a plurality of types of analysis to determine a glucose level measurement. For example, the glucose biosensor 100 may perform a combination of two or more of: a power level analysis, a spectrum analysis, a phase change analysis or a temperature analysis. The glucose biosensor 100 may then average or weight the glucose level measurements determined from each of the plurality of types of analysis to determine a final glucose level measurement. When a difference between two or more of the glucose level measurements are greater than a predetermined threshold (such as a 5% difference), the glucose biosensor 100 may determine that the measurements are in error and perform the testing and analysis again. After repeated errors in the glucose level measurements, the glucose biosensor 100 may request that alternate glucose monitoring methods are performed, such as a finger prick method.

Though three optical fibers 110, 112, 114 are illustrated, the glucose biosensor 100 may employ additional optical fibers. For example, additional optical fibers may be coupled to additional photodetector circuits to detect reflected light 132. Additional optical fibers may also be coupled to additional light source circuits 108 to emit light into the ear canal. For example, a first optical fiber coupled to a first light source circuit 108 may emit light in a first spectrum and a second optical fiber coupled to a second light source circuit 108 may emit light in a second spectrum. In another embodiment, laser control currents may be varied such that a single laser emits electromagnetic radiation at varying frequencies in different spectrums through a single optical fiber.

Using one or methods described herein, the glucose biosensor 100 processes the reflected light 132 to determine a glucose level measurement. When a glucose level measurement reaches a predetermined high or low threshold, the glucose biosensor 100 may transmit an alert message using the wireless transceiver 126. For example, in general, a good range for blood glucose levels is between 70 milligrams/deciliter (mg/Dl) and 150 mg/Dl. When a detected glucose level is lower than 70 or greater than 150, the alert message may trigger a request for an alternate glucose monitoring method be performed to confirm the glucose levels, such as a finger prick method. The alert may also trigger warnings to inject insulin or perform other corrective health measures. In addition, the glucose biosensor 100 may transmit immediate health alerts when a dangerous level of glucose is detected, such as lower than 40 mg/Dl or over 240 mg/Dl. As explained in more detail below, these alerts may be transmitted by the wireless transceiver 126 to a health monitoring gateway that is connected to the Internet. The alerts may be transmitted to a patient's phone, doctor office, caregiver, hospital, pharmacy, etc.

Figure 2:
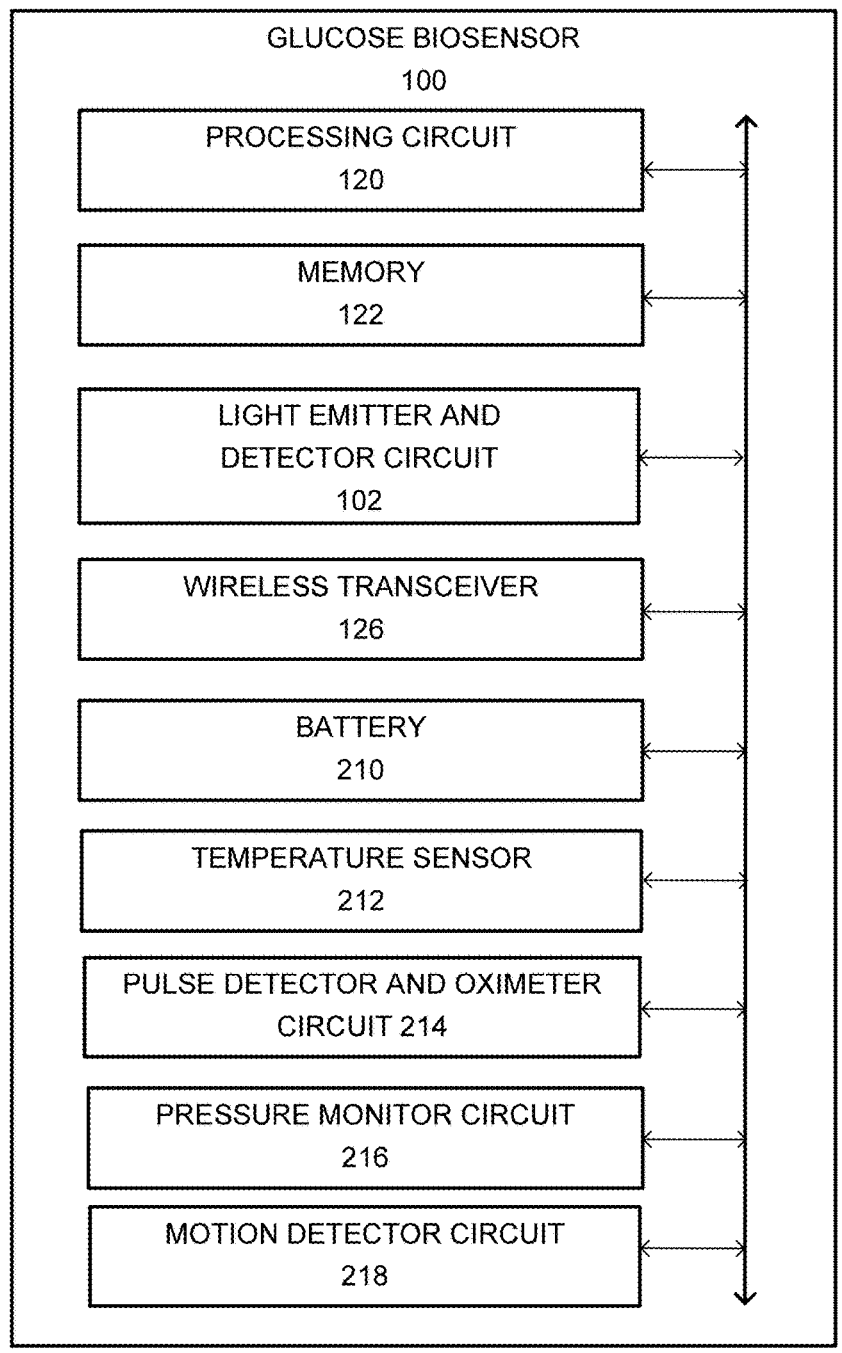
FIG. 2 illustrates a schematic drawing of another exemplary embodiment of a glucose biosensor.

FIG. 2 illustrates another schematic diagram of an embodiment of the glucose biosensor 100. In addition to the light emitter and detector circuit 102, the glucose biosensor 100 may include one or more other biosensors, such as temperature sensor 212, pulse detector circuit and oximeter circuit 214.

The temperature sensor 212 is configured to detect temperature in the outer ear canal. Temperature fluctuations can be indicative of glucose levels in the blood stream or a possible warning of an infection. For example, a detected temperature change over a predetermined threshold may trigger the glucose biosensor 100 to restart glucose monitoring. In an embodiment, the temperature sensor 212 emits an infrared (IR) light signal and process the reflected light 132 to determine a temperature measurement. In another embodiment, the temperature sensor 212 includes an array of sensors (16×16 pixels) positioned within the ear canal to measure discrete temperature changes inside the ear drum. These temperature fluctuations may be used for early prediction of infection or glucose level fluctuations.

The glucose biosensor 100 may also include the pulse detector and oximeter circuit 214. The pulse detector circuit and oximeter circuit 214 includes an infrared (IR) pulse oximeter configured to track a pulse rate and oxygen levels in the blood of the ear canal. In an embodiment, the pulse detector and oximeter circuit 214 may be used to synchronize the pulses of emitted light 130 from the light emitter and detector circuit 102 with higher or maximum blood flow thru the ear canal area. For example, when the IR pulse oximeter detects a pulse of blood or other indicator of a high or maximum blood flow in the ear canal area, it signals the light emitter and detector circuit 102 to initiate a light pulse for detecting glucose levels.

The glucose biosensor 100 may also include the pressure monitor circuit 216. The pressure monitor circuit 216 is configured to monitor blood pressure through the ear canal using IR reflected light. The pressure monitor circuit 216 may provide additional local pressurization information. For example, when the blood pressure is higher, it determines that a higher blood flow is occurring through the ear canal and provides a possible method for a blood pressure reading.

In an embodiment, the glucose biosensor 100 is battery operated and includes a battery 210. To help lower power consumption, in an embodiment, the glucose biosensor 100 includes a motion detector circuit 218 for monitoring activity. For example, the motion detector circuit 218 may include a three-axis accelerometer that measures a position of the patient's head and motion from normal activities. When a patient is still for a predetermined time period, such as during asleep, the motion detector circuit 218 detects little to no movement and signals the glucose biosensor 100 to enter into a rest mode. In the rest mode, the glucose biosensor 100 stops glucose monitoring and other non-essential processing functions. When the motion detector circuit 218 detects movement for another predetermined time period, the motion detector circuit 218 signals the glucose biosensor 100 to exit rest mode and resume monitoring. This activity monitoring feature helps to save power and extend battery life.

In addition, the glucose biosensor 100 may also operate as an activity tracker. The motion detector circuit 218 may determine periods of activity and rest. During such periods of activity and rest, the glucose biosensor 100 determines pulse, oxygen levels, heart rate, core body temperature, glucose readings, etc. The processing circuit 120 may store these measurements with an indicator of activity level in the memory 122. These measurements may be used to track biosensor data during such periods of activity and rest, e.g. in a fitness tracker application.

Figure 3:
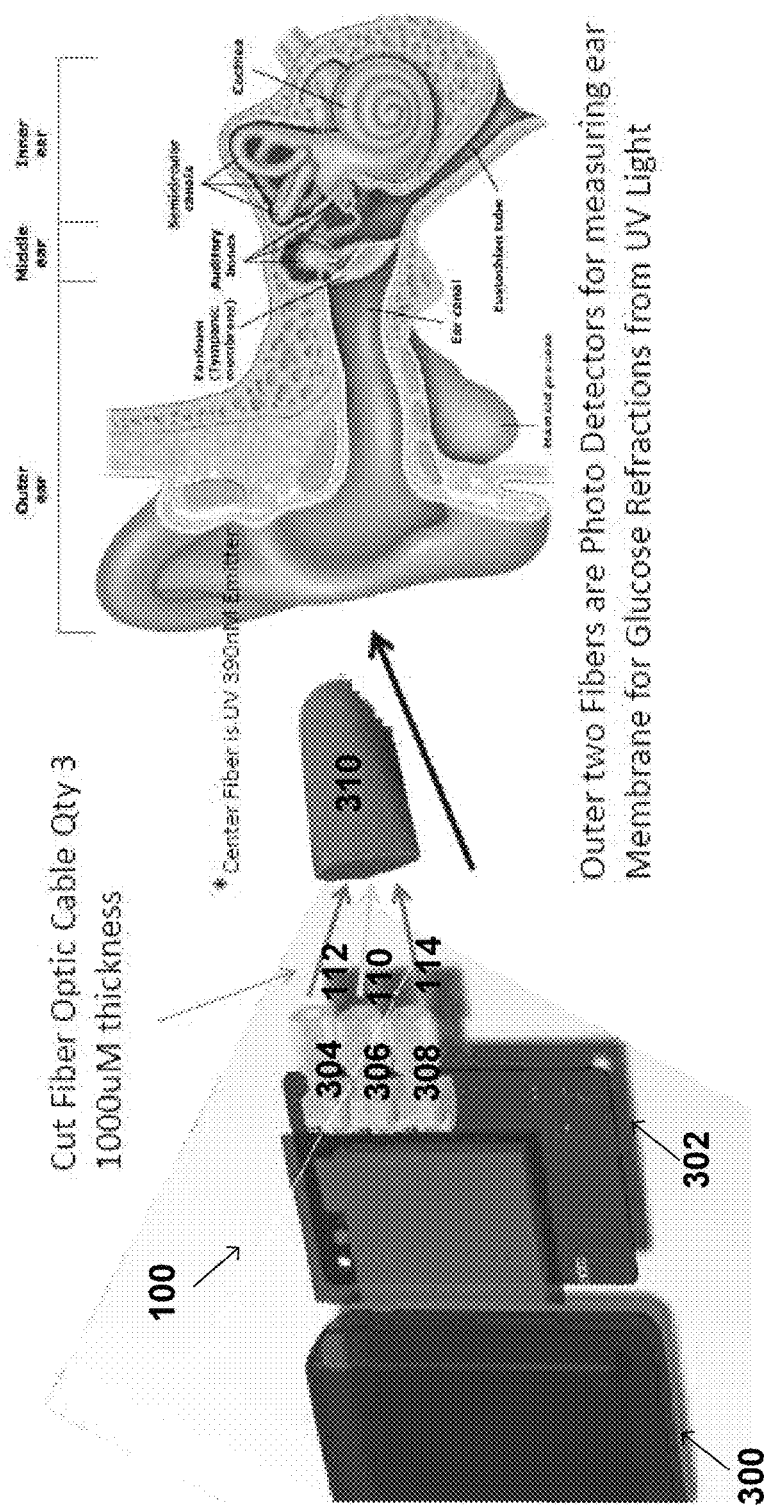
FIG. 3 illustrates a schematic drawing of another exemplary embodiment of a glucose biosensor.

FIG. 3 illustrates a schematic drawing of another exemplary embodiment of the glucose biosensor 100. The glucose biosensor 100 includes an outer casing 300 and one or more printed circuit boards (PCB) 302 that include at least the processing circuit 120, memory 122, wireless transceiver 126 and the light emitter and detector circuit 102. The plurality of optical fibers 110, 112 and 114 are optically coupled to the PCB 302 by a plurality of optical couplers 304, 306 and 308. The plurality of optical fibers 110, 112 and 114 are encased by an earpiece 310. The earpiece 310 is shaped to fit within an outer ear canal. In an embodiment, to help prevent cross contamination, the ear piece 310 or an earpiece cover may be disposable and replaced with a new ear piece 310 or ear piece cover with each use.

Figure 4:
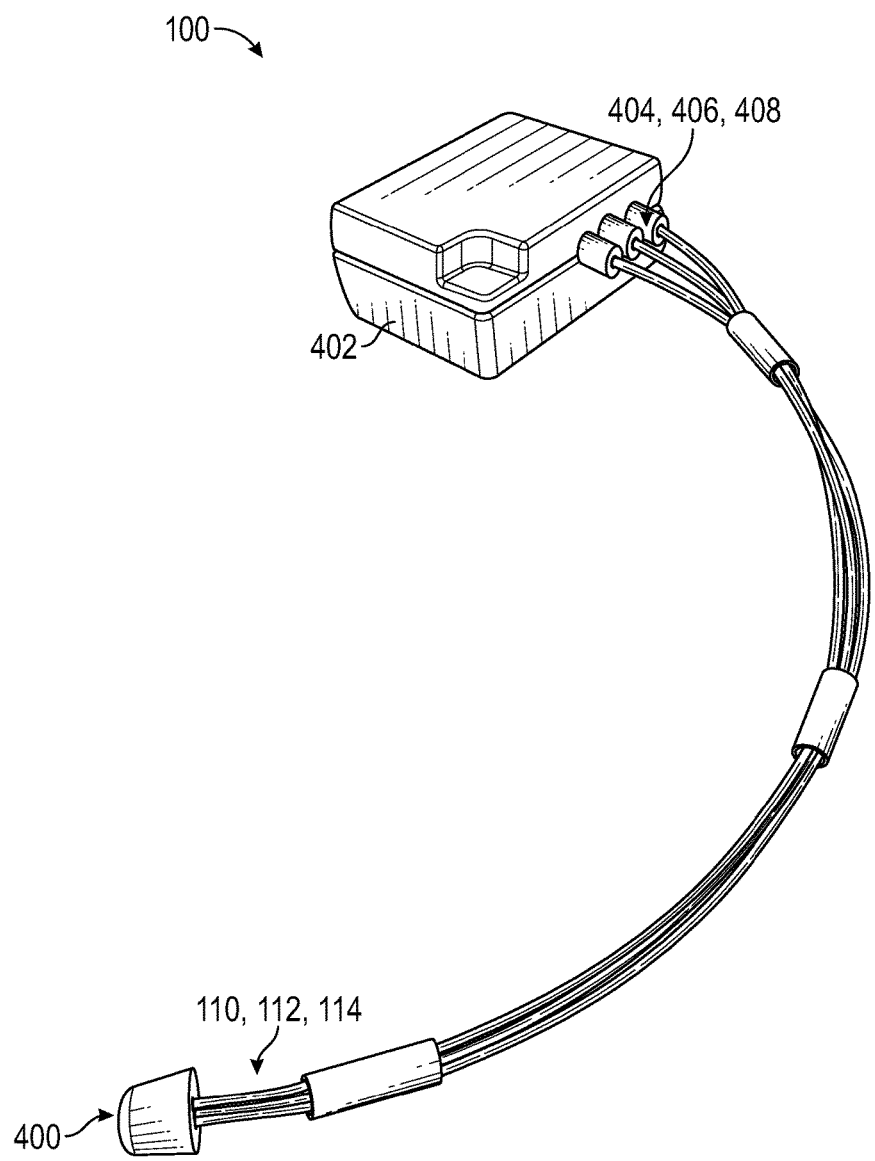
FIG. 4 illustrates a schematic drawing of another exemplary embodiment of a glucose biosensor.

FIG. 4 illustrates a schematic drawing of another exemplary embodiment of a glucose biosensor 100. This embodiment of the glucose biosensor 100 includes the plurality of optical fibers 110, 112 and 114 and an earpiece 400. The plurality of optical fibers 110, 112, 114 are optically coupled to the glucose biosensor 100 by the plurality of optical couplers 404, 406, 408. In an embodiment, the plurality of optical fibers 110, 112 and 114 are preferably sized such that a casing 402 of the glucose biosensor 100 may be held while the earpiece 400 is positioned within the outer ear canal. For example, the plurality of optical fibers 110, 112, 114 may be two to three feet long with a 1000 uM thickness.

Figure 5:
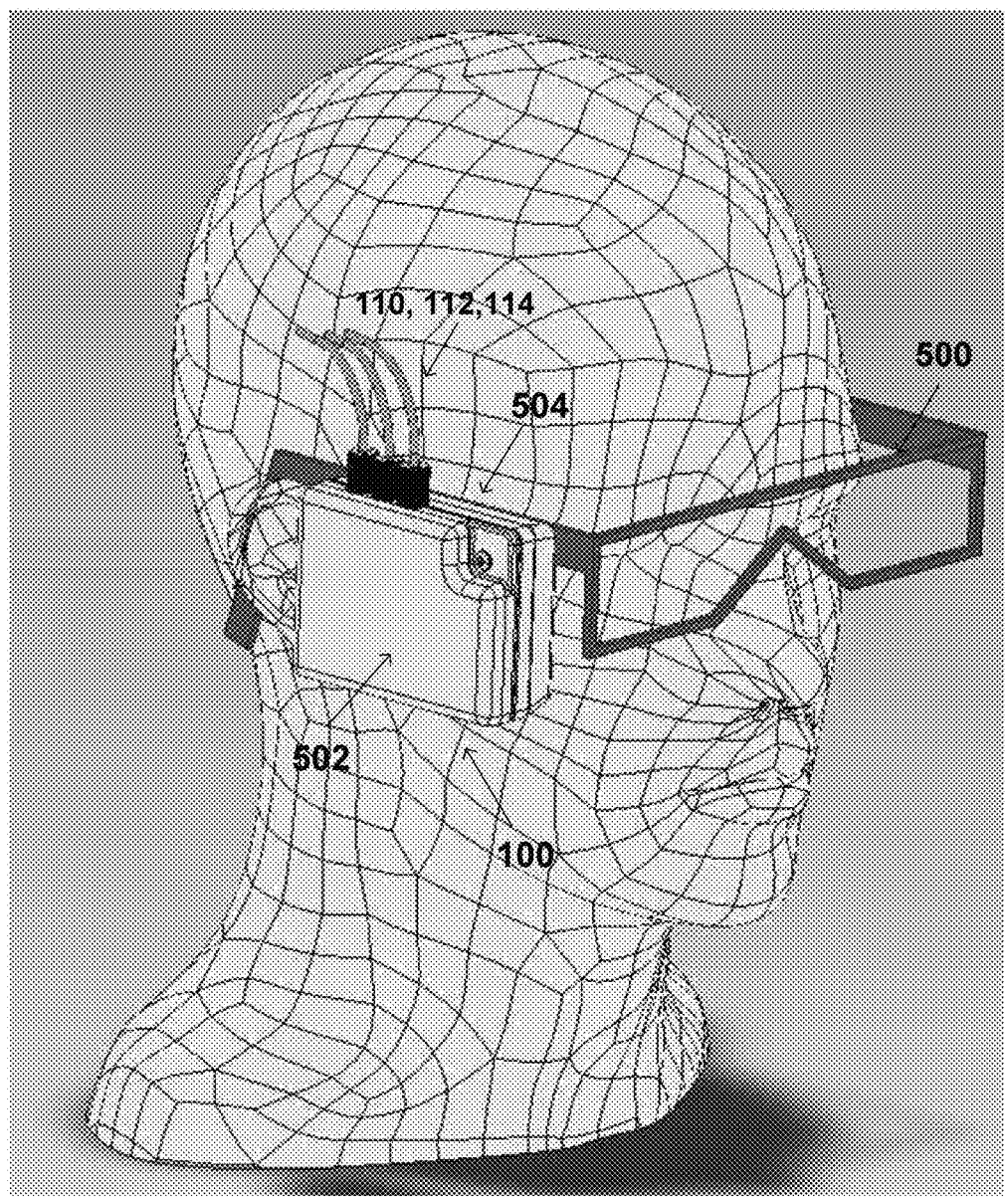
FIG. 5 illustrates a schematic drawing of an exemplary embodiment of a casing of a glucose biosensor.

FIG. 5 illustrates a schematic drawing of another exemplary embodiment of a casing 502 for the glucose biosensor 100. In this embodiment, the casing 502 of the glucose biosensor 100 is configured to attach to an eye glass frame 500. For example, the glucose biosensor 100 includes a clip or other fastener that attaches to a temple 504 of the eye glass frame 500. The optical fibers 110, 112, 114 may then be positioned in the ear canal without needing to hold the glucose biosensor 100.

Figure 6:
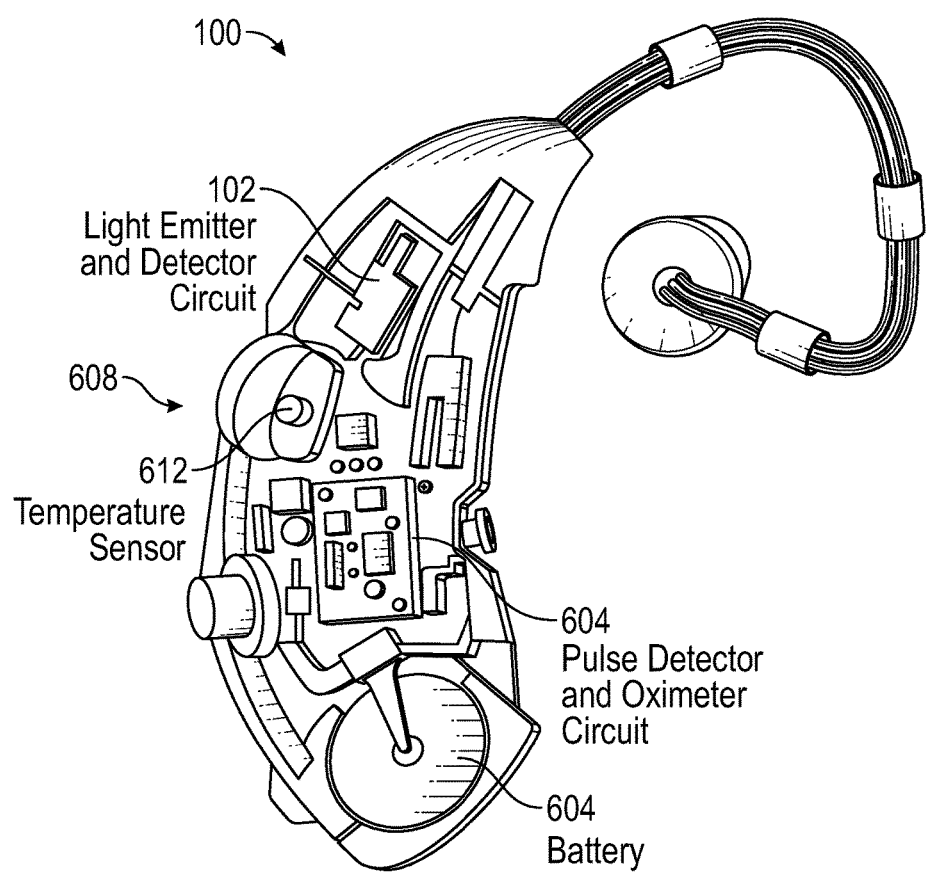
FIG. 6 illustrates is schematic drawing of another exemplary embodiment of a glucose biosensor.

FIG. 6 illustrates a schematic drawing of another exemplary embodiment of a glucose biosensor 100. In this embodiment, the glucose biosensor 100 is configured as an earpiece 608 shaped to rest around the outer ear. The plurality of optical fibers 110, 112, 114 lead from the earpiece 608 to an earbud 600. The ends of optical fibers 110, 112, 114 are encased in the earbud 600. The earbud 608 may then be positioned into an outer ear canal. The earbud 600 may be fabricated from rubber or plastic. The glucose biosensor 100 also includes a battery 602. For example, the battery 602 may be a replaceable lithium battery or a rechargeable battery.

Since the ear membrane is thin at the back of the ear, a pulse detector and oximeter circuit 604 may be positioned to detect pulse and oxygen levels from the back of the ear rather than from the ear canal. A temperature sensor 612 may also be positioned on the glucose biosensor 100 to detect temperature from membranes on the back of the ear.

In another embodiment, the glucose biosensor 100 may be attached to or included within a headphone style mechanical interface. The headphone style mechanical interface provides comfort while performing glucose measurements.

In another exemplary embodiment, the glucose biosensor 100 is encapsulated in a swallowable pill form factor with a wireless transceiver. The pill is ingestible and may employ a similar UV fluorophores technique described herein or other techniques to measure glucose level measurements. The glucose level measurements are transmitted using the wireless transceiver. For example, the ingestible pill transmits a UV, visible or IR light and measures the internally reflected light to determine glucose levels. The ingestible pill wirelessly transmits the glucose measurements to a gateway 1100 or glucose meter 1200 outside the body.

Figure 7:
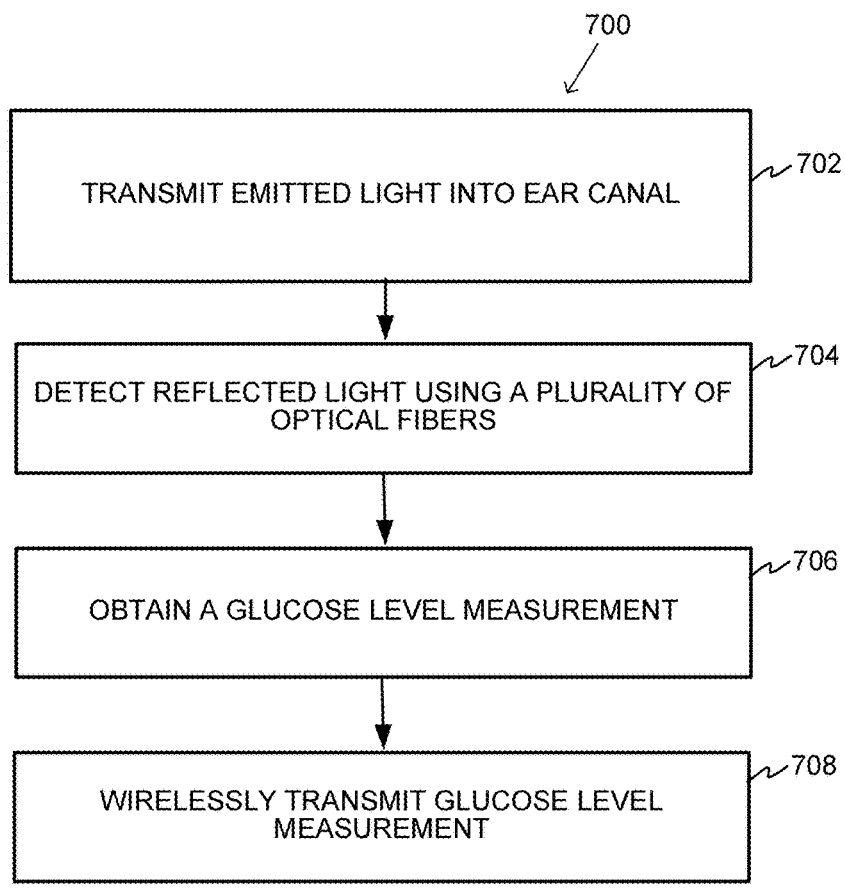
FIG. 7 illustrates a logical flow diagram of an exemplary method for determining a glucose level measurement.

FIG. 7 illustrates a logical flow diagram of an exemplary method 700 for glucose monitoring. A light pulse (either UV, visible or IF or a combination thereof) is emitted by a light source circuit and transmitted by at least one optical fiber into an ear canal. The reflected light is captured by a plurality of optical fibers, wherein each of the plurality of optical fibers transmits the reflected light to a photodetector circuit. For example, a first optical fiber and a second optical fiber capture the reflected light. The reflected light captured by the first optical fiber is detected by a first photodetector circuit, and the reflected light captured by the second optical fiber is detected by a second photodetector circuit 704. The reflected light is processed and a glucose level measurement is obtained 706. The glucose level measurement is then wirelessly transmitted to a gateway or glucose meter or user device 708.

Figure 8:
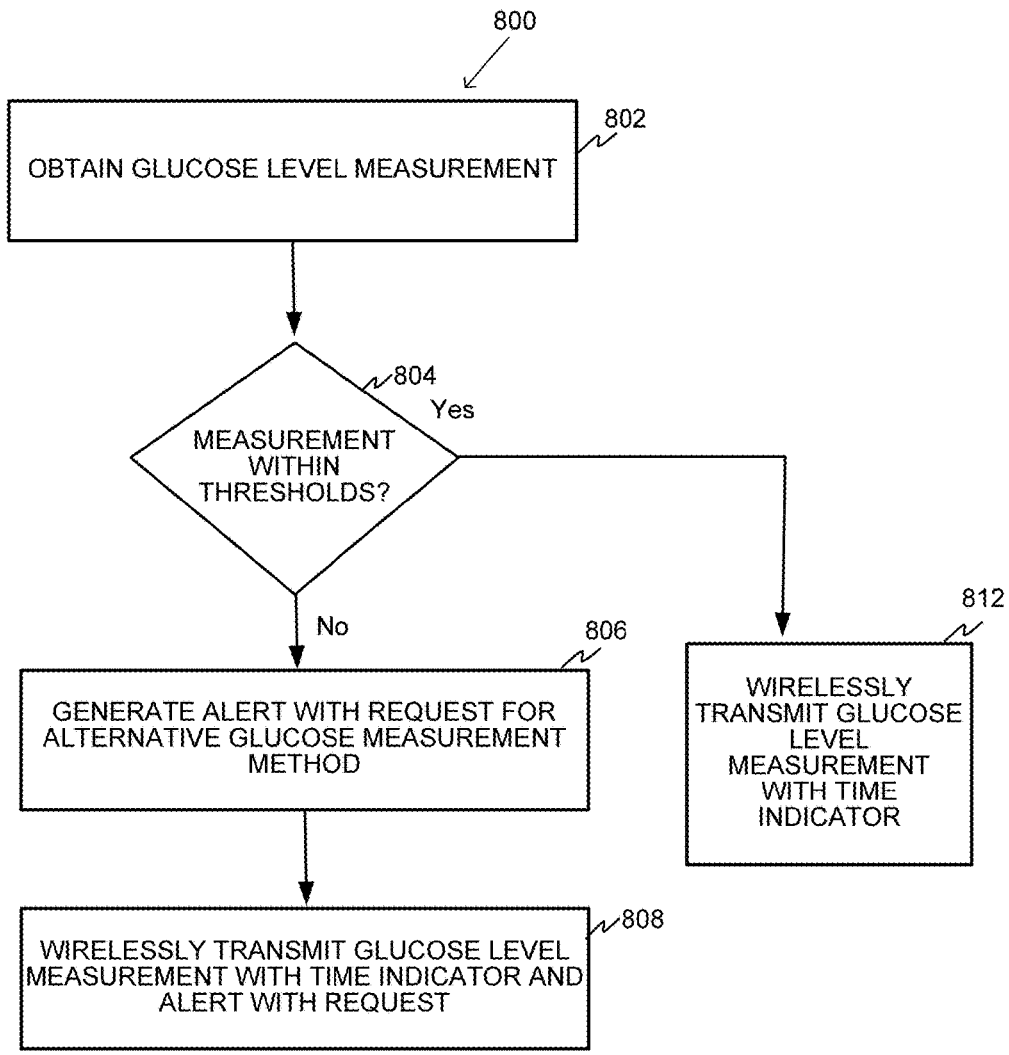
FIG. 8 illustrates a logical flow diagram of an exemplary method for glucose monitoring in more detail.

FIG. 8 illustrates a logical flow diagram of an exemplary method 800 for glucose monitoring in more detail. As explained hereinabove, the glucose biosensor 100 obtains a glucose level measurement 802. The glucose level measurement is compared with normal ranges, and it is determined whether the glucose level measurement is within predetermined thresholds 804. The thresholds may be configured specifically for the authorized user of the glucose biosensor 100 or based on general guidelines for safe ranges of glucose levels in the bloodstream. For example, in general, a safe range for glucose levels is between 70 milligrams/deciliter (mg/Dl) and 150 mg/Dl. When the glucose level measurements are within the predetermined thresholds, the glucose level measurements are wirelessly transmitted with a time indicator 812.

When the glucose level measurements are not within the predetermined thresholds, an alert is generated with a request for another glucose test using an alternative method, such as a finger prick method 806. The alternative method provides a second test for glucose levels to determine whether the glucose measurement obtained by the glucose biosensor is accurate or whether an error has occurred. The second test may be performed prior to any corrective measures (such as insulin injection, etc.). The glucose level measurement and alert with request are wireless transmitted to a gateway or glucose meter or user device 808. For example, when the glucose measurement is lower than 70 mg/Dl or greater than 150 mg/Dl, the alert message may include a request for an alternate glucose monitoring method be performed to confirm the glucose levels, such as a finger prick method. The alert may also trigger warnings to inject insulin or perform other corrective health measures. In addition, the glucose biosensor 100 may transmit immediate health alerts when a dangerous level of glucose is detected, such as lower than 40 mg/Dl or over 240 mg/Dl, with a message advising that the patient perform certain corrective measures, such as injection of insulin. The immediate health alert may be transmitted to a gateway, glucose meter, a user device, doctor's office, or other contact person as well.

Figure 9:
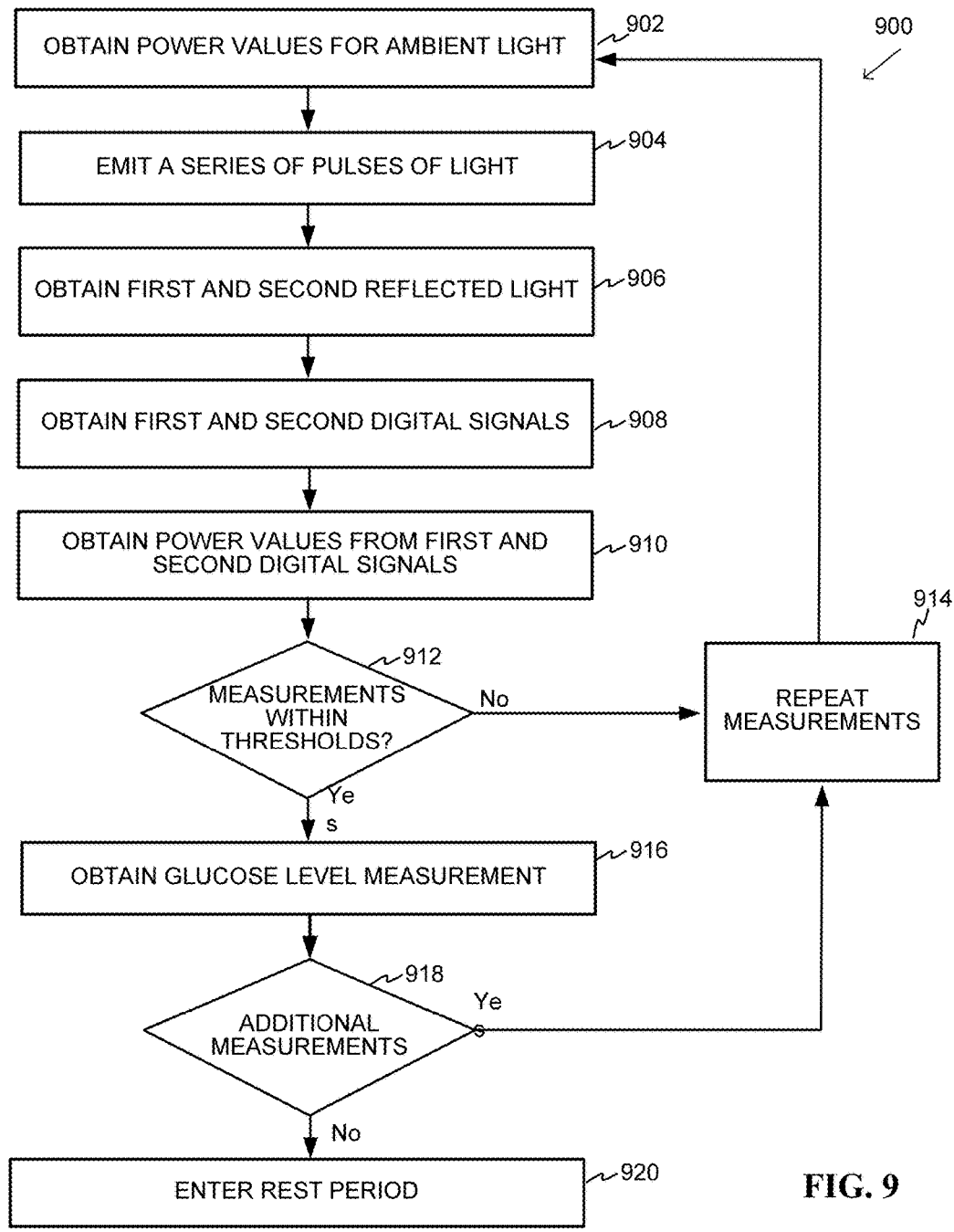
FIG. 9 illustrates a logical flow diagram of an exemplary method for obtaining a glucose level measurement.

FIG. 9 illustrates a logical flow diagram of an exemplary method 900 for obtaining a glucose level measurement. To cancel out any foreground noise, power values for ambient light in the ear canal are first obtained 902. For example, prior to emission of a light pulse, ambient light is captured by a first optical fiber and transmitted to a first photodetector circuit. The first photodetector circuit transmits the detected light signal to an A/D converter circuit that generates a first digital signal. From the sampled first digital signal, the minimum, maximum and peak power values of the ambient light are calculated, e.g. using an integral equation of energy. The power values for the ambient light from the first optical fiber are stored in memory, represented herein as A1. Similarly, prior to a light pulse, the ambient light captured by a second optical fiber is detected by a second photodetector and an A/D converter circuit generates a second digital signal. From the second digital signal, the minimum, maximum and peak power values are calculated, e.g. using an integral equation of energy. The power values for the ambient light from the second optical fiber are stored in memory, represented herein as A2.

Next, a light pulse, e.g. of approximately 10 ms, is emitted 904, and the reflected light from a first optical fiber is detected by a first photodetector circuit to generate a first detected light and the reflected light from a second optical fiber is detected by a second photodetector circuit that generates a second detected light. The first photodetector circuit transmits the first detected light to a first A/D converter that generates a first digital signal, and the second photodetector circuit transmits the second detected light to either the first A/D converter or to a second A/D converter to generate a second digital signal 906. The minimum, maximum and peak power levels of the first digital signal, represented herein as B1, and the second digital signal, represented herein as B2, are obtained 908.

The current measurements of the power levels are then compared with previous measurements 912. When the current measurements are not within a predetermined threshold, e.g. a difference greater than 30% from previous measurements, then the current measurements are ignored, and the measurements are repeated 914. When the current measurements are within a predetermined threshold, a glucose level measurement is obtained using the current measurements 916.

An exemplary process for calculating a glucose level measurement is now explained through other methods and calculations may also be implemented. A differential value is calculated between the power levels derived from the reflected light B1, B2 and the foreground noise A1, A2. For example, a differential channel equation is used to cancel out the power levels obtained from the detected ambient light A1, A2 from the power levels obtained using the reflected light B1, B2:

$$\text{Sum} = (B1-A1) - \text{ABS}(B2-A2), \text{ where ABS is the absolute value.}$$

The above Sum is calculated for a plurality of samples over a short period, e.g. ~10 ms, and the partial integral of the Sums of the samples is calculated to generate an interim value. A bit shifting is performed on the interim value for scaling purposes. For example, the interim value is right shifted to reduce resolution to allow for small integer numbers like 50-300 mg/Dl. An individual offset may also be applied, as determined in a calibration process described in more detail with respect to FIG. 10, to obtain the glucose level measurement 916.

Another exemplary process for calculating a glucose level measurement is based on a phase change. For example, the samples B1, B2 of the reflected light have wavelength information as well. In an embodiment, a phase change between the emitted light and the samples B1 and B2 is determined. For example, using a fast sample A/D conversion, phase information for the samples B1 and B2 are stored in a matrix. The phase information is compared to the emitted light from the light source. The phase response curves for each channel, e.g. each photodetector, is then determined. A glucose level measurement is then determined based on the phase response curves.

Though two exemplary processes for calculating a glucose level measurement is described herein, e.g. one using power levels and the other based on phase changes, other methods and calculations may also be implemented. In addition, both these exemplary processes may be implemented in combination to obtain a glucose level measurement 916.

Next, the process then determines whether additional measurements are scheduled 918. For example, in an embodiment, the process is repeated over three 10 ms intervals followed by a 30-60 second rest period. When additional measurements are scheduled, the measurements are repeated 914. When additional measurements are not scheduled, the process enters a rest period 920.

Figure 10:
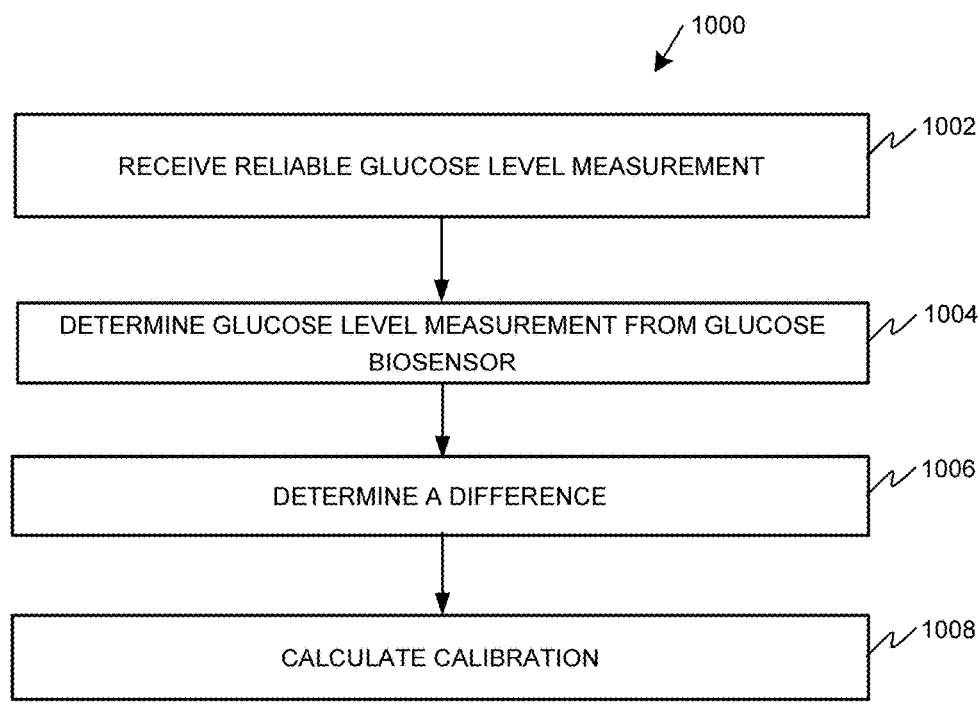
FIG. 10 illustrates a logical flow diagram of an embodiment of an exemplary method for calibrating the glucose biosensor.

FIG. 10 illustrates a logical flow diagram of an embodiment of an exemplary method 1000 for calibrating the glucose biosensor 100 for glucose monitoring. A reliable glucose level measurement is received 1002. For example, a finger prick method may be used with a glucose meter to determine a glucose level. This measurement is wirelessly transmitted to the glucose biosensor 100 by the glucose meter or a gateway. A glucose level measurement is then obtained by the glucose biosensor from the ear canal 1004. The ear canal measurement is compared with the reliable measurement. An absolute difference or a percentage difference is determined 1006. This process may be repeated a number of times. Based on the determined difference, a calibration is calculated 1008. This calibration is used by the glucose biosensor 100 to adjust the glucose level measurement from the ear canal, e.g. as described above with respect to FIG. 9.

Gateway

Figure 11:
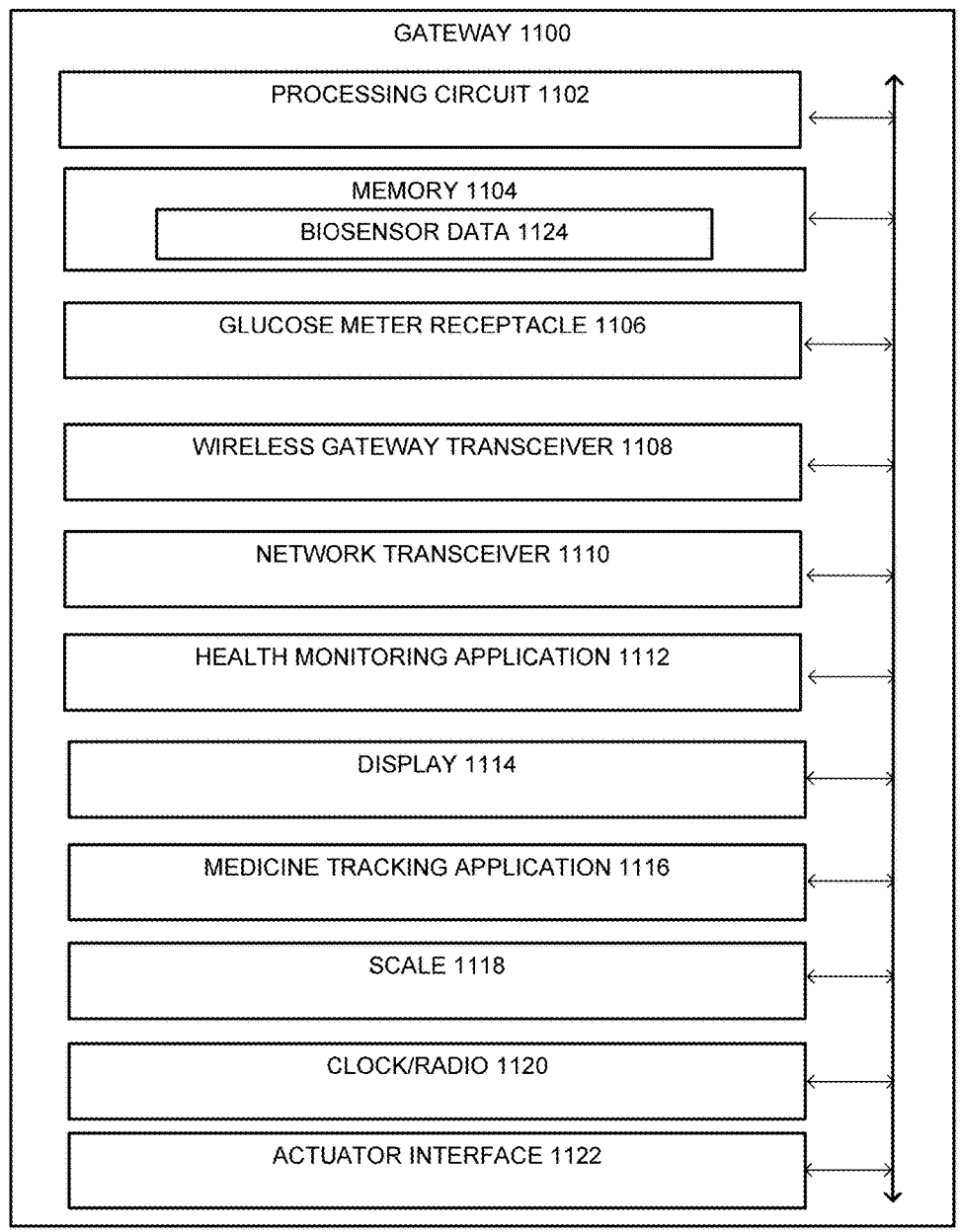
FIG. 11 illustrates a schematic drawing of an exemplary embodiment of a gateway.

FIG. 11 illustrates a schematic drawing of an exemplary embodiment of a gateway 1100. The gateway 1100 includes a processing circuit 1102 and a memory 1104. For example, the memory 1104 is a non-transitory, processor readable medium that stores instructions which when executed by the processing circuit 1102, causes the processing circuit 1102 to perform one or more functions described herein. The memory 1104 may also store biosensor data 1124 from the glucose biosensor 100.

The gateway 1100 includes a wireless gateway transceiver 1108 operable to wirelessly communicate with the glucose biosensor 100. For example, the wireless gateway transceiver 1108 may operate in the 900 MHz range over a serial link using a proprietary protocol or may utilize a standard protocol, such as IEEE 802.11ah, IEEE 802.15-11, or Zigbee, to communicate with the glucose biosensor 100. In other embodiments, the wireless gateway transceiver 1108 may operate in one or more other wireless frequency bands or protocols, such as near field communication, short range radio frequency, RFID, infrared link, Bluetooth, or other short range wireless communication protocol, to communicate with the glucose biosensor 100.

The gateway 1100 receives packets with biosensor data 1124, including glucose level measurements, from the glucose biosensor 100 using the wireless gateway transceiver 1108. The gateway 1100 stores and tracks the biosensor data 1124. When two or more authorized patients are operating biosensors, the wireless gateway transceiver 1108 may request to receive patient ID information in the data packets with the biosensor data 1124. The gateway 1100 is then operable to store and track biosensor data 1124 associated with two or more patients.

The gateway 1100 further includes a network transceiver 1110 that is operable to communicate either wirelessly or through a wired connection over a wide area network (WAN), such as the Internet, to a doctor's office, hospital, pharmacy, caregiver, user device or a device of another authorized user. The gateway 1100 may further communicate with a central application server over the WAN that provides health monitoring services. The gateway 1100 may communicate biosensor and patient data to the central application server for access by a user device, such as a smart phone, laptop, desktop, smart tablet, etc., as described in more detail herein. The gateway 1100 further includes a display 1114. The display 1114 may be a touch screen.

In an embodiment, the gateway 1100 is operable to support a health monitoring application 1112. The health monitoring application 1112 may be a web-based application supported by a central application server. For example, the central application server may be a web server and support the health monitoring application 1112 via a website. The gateway 1100 may then use a web browser or other HTML enabled application to access either all or parts of the health monitoring application 1112 via the website. The health monitoring application 1112 is then run within the web browser. In another embodiment, the health monitoring application 1112 is a stand-alone application that is downloaded to the gateway 1100 and is operable on the gateway 1100 without access to a web server or only needs to accesses a web server for additional information, such as biosensor data.

Using the health monitoring application 1112, the gateway 1100 is configured to provide a graphical user interface (GUI) for the display 1114. An authorized user is operable to track biosensor data 1124 using the health monitoring application 1112 and control certain functions of the glucose biosensor 100. For example, the health monitoring application 1112 may generate a GUI that includes a graphical selection of commands for controlling the glucose biosensor 100, such as a rest mode command or re-calibrate command. The authorized user may input commands to control the operation of the glucose biosensor 100 or other biosensors.

In other methods, the gateway 1100 may include voice interactive capabilities to communicate alerts and receive data or commands.

In addition, the health monitoring application 1112 may generate a GUI that includes a graphical display of glucose levels or other biosensor data 1124 over a requested period of time, such as one day, one week, etc. The health monitoring application 1112 may issue alerts when biosensor data 1124 reaches certain predetermined thresholds. For example, when a blood glucose level reaches a predetermined high or low threshold, the gateway 1100 displays an alert and sounds an alert message. In general, a good range for blood sugar levels is between 70 milligrams/deciliter (mg/Dl) and 150 mg/Dl. When the sugar level are lower than 70 mg/Dl or greater than 150 mg/Dl, the alert message may include a request for an alternate glucose monitoring method be performed to confirm the glucose levels, such as a finger prick method. The alert may also trigger warnings to inject insulin or perform other corrective health measures. In addition, the glucose biosensor 100 may transmit immediate health alerts when a dangerous level of glucose is detected, such as lower than 40 mg/Dl or over 240 mg/Dl. The immediate health alert may be transmitted to a user device, doctor's office, or other contact person as well.

The gateway 1100 may also generate a GUI that allows a user to input data, such as glucose measurements determined by the finger prick method. Such measurements may be communicated back to the glucose biosensor 100 for calibration using the wireless gateway transceiver 1108.

In another example, the gateway 1100 generates a GUI that allows a user to input when a meal is consumed by the patient. Since glucose targets depend on timing of meals, this information may be used in the tracking and charting of glucose levels. For example, the American Diabetes Association suggests the following targets for most nonpregnant adults with diabetes. More or less stringent glycemic goals may be appropriate for each individual: Before a meal (preprandial plasma glucose): 80-130 mg/dl and 1-2 hours after beginning of the meal (Postprandial plasma glucose): Less than 180 mg/dl.

The gateway 1100 may also generate a GUI that includes an activity tracker display. The activity tracker display may include periods of rest or sleep and periods of activity along with biosensor data for such periods, such as pulse, glucose levels, oxygen levels, temperature, blood pressure, etc. One or more of these functions of the health monitoring application 1112 described with respect to the gateway may also be accessed by a user device using a web-based application supported by the central application server as discussed in more detail herein.

The gateway 1100 may also include an integrated blood glucose meter or a glucose meter receptacle 1106 for interfacing with a blood glucose meter. For example, the glucose meter may be used in the finger prick method to determine blood glucose levels. In an embodiment, the glucose level measurement from the glucose biosensor 100 is used as an indicator, e.g. for tracking and charting glucose levels over a period of time, while readings from the glucose meter using test strips (e.g. finger prick method) are used for more accurate measurements or verification. For example, the glucose level measurements of the glucose meter are used for verification of the glucose level measurements of the glucose biosensor 100.

The gateway 1100 may include a medicine bottle receptacle 1008. The medicine bottle receptacle is configured to hold a medicine bottle that includes, e.g., glucose test strips. In the finger prick method, the patient must then prick a clean fingertip with a special needle (lancet) to draw a drop of blood. The test strip is then touched to the drop of blood and inserted into the glucose meter. The glucose meter determines the blood glucose level and displays the measurement on its screen or on the display 1114 of the gateway 1100. When used and stored properly, blood glucose meters are generally accurate in measuring glucose levels. Thus, the finger prick method provides a good verification of the glucose biosensor 100 measurements.

In an embodiment, the gateway 1100 includes a medicine tracking application 1116 and a scale 1118 as part of the medicine bottle receptacle. The scale 1118 weighs the medicine bottle, and based on the weight, the medicine tracking application 1116 determines a number of available test strips. When the detected number of test strips falls below a threshold, the medicine tracking application 1116 may issue an alert to re-order test strips, such as provide a GUI on the display 1114 with alert message of the low medication. In another embodiment, the gateway 1100 may communicate with a pharmacy to request a refill. In another embodiment, the gateway 1100 may communicate with a doctor's office to request a new prescription. The medicine tracking application 1116 thus tracks the weight of a medicine bottle or other receptacle and triggers an alert when the weight reaches a predetermined threshold, e.g. indicating that the medicine needs to be refilled.

The gateway 1100 in an exemplary embodiment may also include an alarm clock and/or a radio 1120. The gateway 1100 may also include an actuator interface 1122 for use with a regulated insulin pump or artificial pancreas. The gateway 1100 may receive a glucose level measurement from the glucose biosensor 100 or from a glucose meter and process the measurement to control a regulated insulin reservoir (such as an insulin pump or artificial pancreas) in implants or automatic insulin control system.

Figure 12:
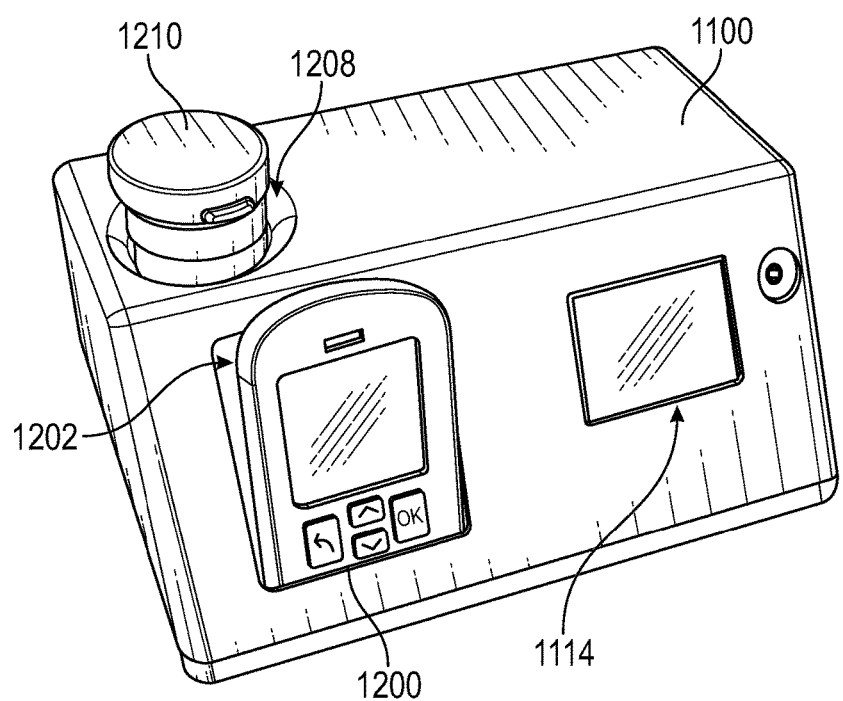
FIG. 12 illustrates a schematic block diagram of another exemplary embodiment of a gateway.

FIG. 12 illustrates a schematic block diagram of an exemplary embodiment of the gateway 1100. The gateway 1100 in this embodiment includes a glucose meter receptacle 1202 configured to interface with a stand-alone glucose meter 1200. In another embodiment, the gateway 1100 may include an integrated glucose meter 1200. The gateway 1100 in this illustration includes the medicine bottle receptacle 1208 with a medicine bottle 1210 situated therein. The gateway 1100 also includes the display 1114 configured to display one or more of the GUI's described herein with respect to the health monitoring application 1112 or medicine tracking application 1116. The gateway 1100 may also include the clock and/or radio 1120.

Figure 13:
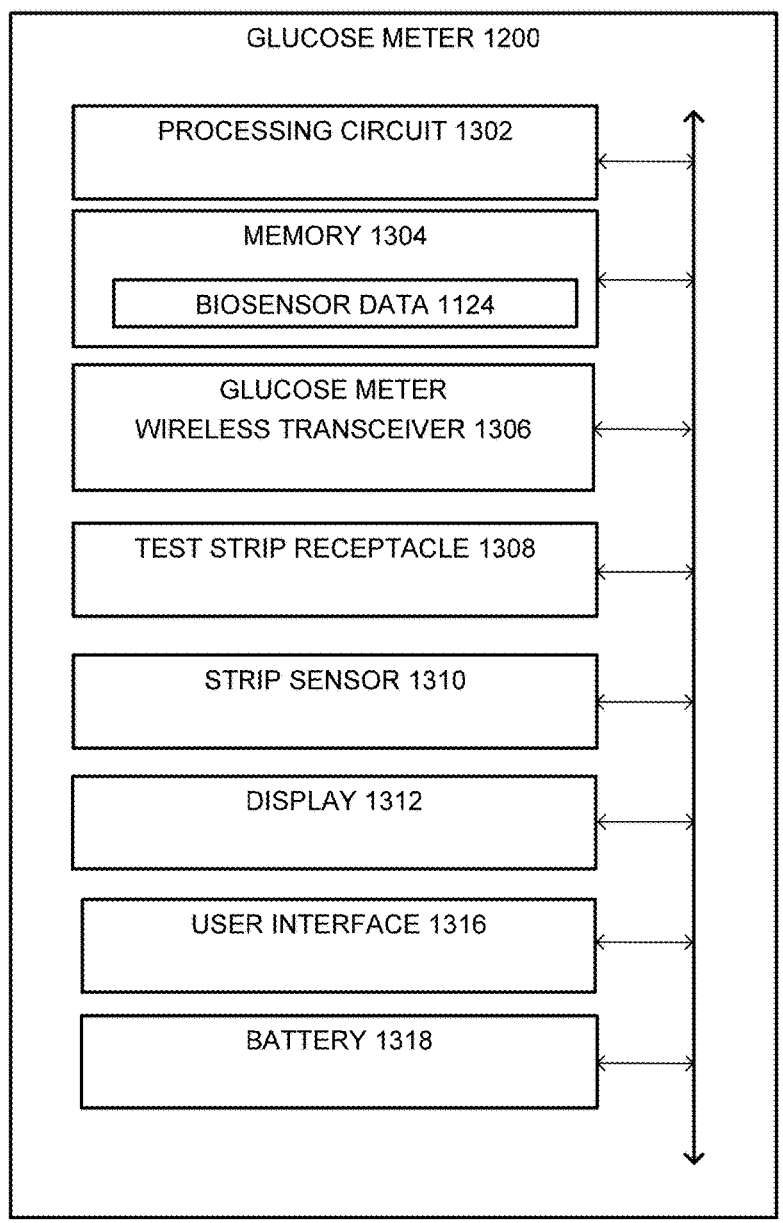
FIG. 13 illustrates a schematic block diagram of an exemplary embodiment of a glucose meter.

FIG. 13 illustrates a schematic block diagram of an exemplary embodiment of the glucose meter 1200. The glucose meter 1200 includes a processing circuit 1302 and a memory 1304. For example, the memory 1304 is a non-transitory, processor readable medium that stores instructions which when executed by the processing circuit 1302, causes the processing circuit 1302 to perform one or more functions described herein. The memory 1304 may also store biosensor data 1124 from the glucose biosensor 100 or generated by the glucose meter 1200 itself.

When the glucose meter 1200 is not integrated with the gateway 1100, the glucose meter 1200 may include a wireless transceiver 1306 operable to wirelessly communicate with the glucose biosensor 100 and/or the gateway 1100. For example, the wireless transceiver 1306 may operate in the 900 MHz range over a serial link using a proprietary protocol or may utilize a standard protocol, such as IEEE 802.11ah, IEEE 802.15-11, or Zigbee, to communicate with the glucose biosensor 100 or the gateway 1100. In other embodiments, the wireless transceiver 1306 may operate in one or more other wireless frequency bands or protocols, such as near field communication, short range radio frequency, RFID, infrared link, Bluetooth, or other short range wireless communication protocol, to communicate with the glucose biosensor 100 or the gateway. The glucose meter 1200 receives packets with biosensor data 1124, including glucose level measurements, from the glucose biosensor 100 or the gateway 1100 using the wireless transceiver 1306. In addition, the glucose meter 1200 transmits packets with biosensor data, including glucose level measurements, to the gateway 1100. The glucose meter 1200 may also receive glucose level measurements directly from the glucose biosensor 100 or indirectly through the gateway 1100 and store the data for tracking and display. For example, the glucose meter 1200 may track and display the time and date of a test, the result, and graph trends over time.

The glucose meter 1200 may also communicate with the glucose biosensor 100 to transmit glucose level measurements to the glucose biosensor 100. In an embodiment, the glucose level measurements from the glucose biosensor 100 are used as an indicator, e.g. for tracking and charting glucose levels over a period of time, while readings from the glucose meter 1200 are used for verification since the measurements from the glucose meter 1200 may be more accurate or exact. In another embodiment, as described in FIG. 10, the glucose meter 1200 is used for calibrating measurements by the glucose biosensor 100.

The glucose meter 1200 further includes a test strip receptacle 1308 and a strip sensor 1310. In the finger prick method, the patient must prick a clean fingertip with a special needle (lancet) to draw blood. The test strip is then touched to the blood and inserted into the test strip receptacle 1308 of the glucose meter 1200. The strip sensor 1310 determines the blood glucose level from the test strip and displays the measurement on display 1312 or on the display 1114 of the gateway 1100. The glucose meter 1200 may further include a user interface 1316, such as a keypad, to control operation and the display 1312 of the glucose meter 1200. The glucose meter 1200 may be battery operated and include a battery 1318.

One or more functions described herein as being performed by the glucose meter 1200 may be performed by the gateway 1100. Alternatively, one or more functions described herein as being performed by the gateway 1100 may be performed by the glucose meter 1200.

Communication Network

Figure 14:
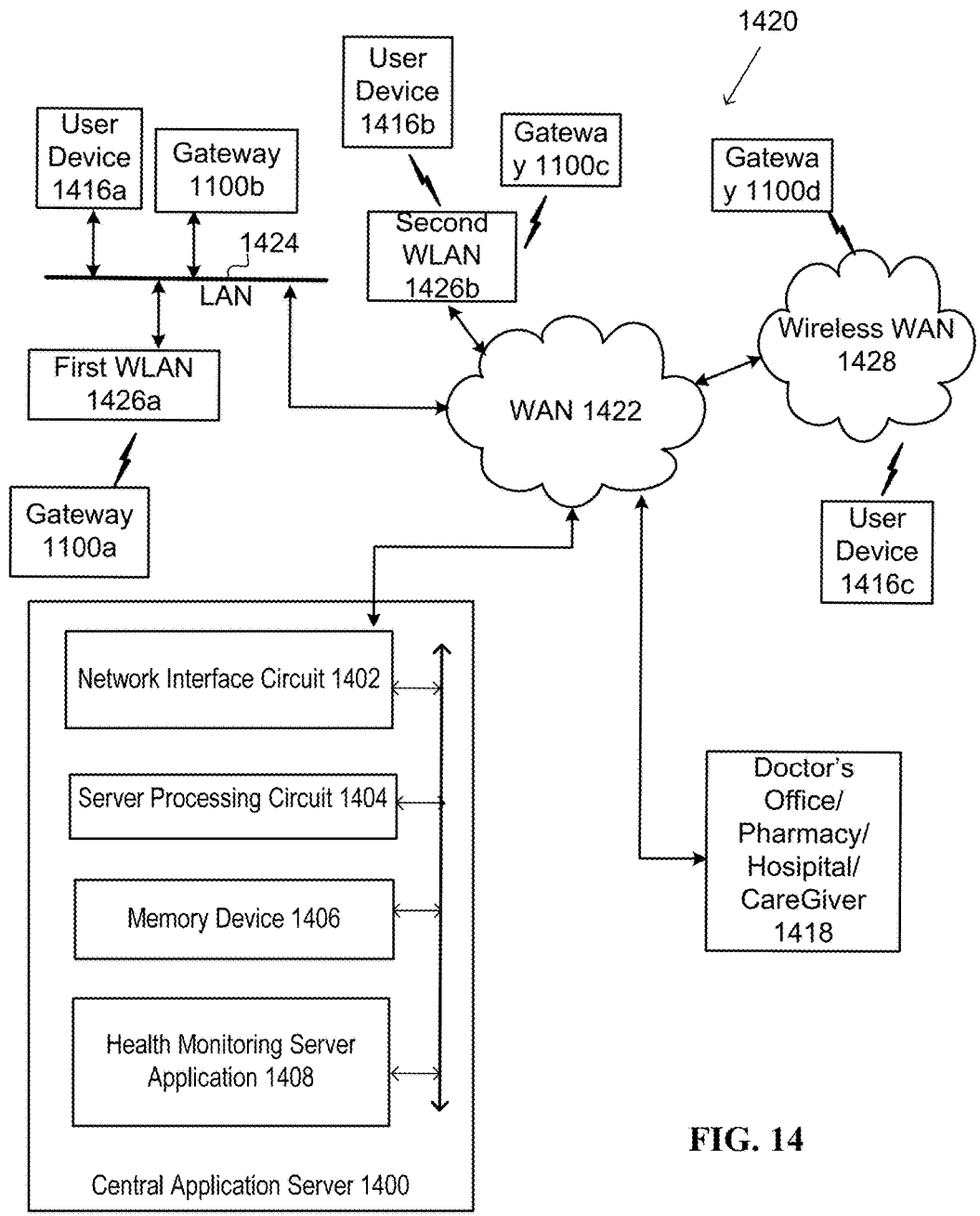
FIG. 14 illustrates a schematic block diagram of an exemplary embodiment of an exemplary communication network in which the devices described herein may operate.

FIG. 14 illustrates a schematic block diagram of an embodiment of an exemplary communication network 1420 in which the devices described herein may operate. The exemplary communication network 1420 includes one or more networks that are communicatively coupled, such as a wide area network (WAN) 1422, a local area network (LAN) 1424, a first wireless local area network (WLAN) 1426a, a second WLAN 1426b, and a wireless wide area network (WAN) 1428. The LAN 1424 and the first and second WLANs 1426a and 1426b may operate inside a home or enterprise environment, such as a doctor's office, pharmacy or hospital or other caregiver or business. The wireless WAN 1428 may include, for example, a 3G or 4G cellular network, a GSM network, a WIMAX network, an EDGE network, a GERAN network, etc. or a satellite network or a combination thereof. The WAN 1422 includes the Internet, service provider network, other type of WAN, or a combination of one or more thereof.

One or more gateways 1100a, 1100b, 1100c, 1100d are communicatively coupled to a central application server 1400 by one or more of the exemplary networks in the communication network 1420. The central application server 1400 includes a network interface circuit 1402 and a server processing circuit 1404. The network interface circuit 1402 includes an interface for wireless and/or wired network communications with one or more of the exemplary networks in the communication network 1420. The network interface circuit 1402 may also include authentication capability that provides authentication prior to allowing access to some or all of the resources of the central application server 1400. The network interface circuit 1402 may also include firewall, gateway and proxy server functions.

The central application server 1400 also includes a server processing circuit 1404 and a memory device 1406. For example, the memory device 1406 is a non-transitory, processor readable medium that stores instructions from the health monitoring server application 1408 which when executed by the server processing circuit 1404, causes the server processing circuit 1404 to perform one or more functions described herein. In an embodiment, the memory device 1406 stores biosensor data for a plurality of patients transmitted to the central application server 1400 from the plurality of gateways 1100a-d.

The central application server 1400 includes a health monitoring server application 1408. The health monitoring server application 1408 is operable to communicate with the plurality of gateways 1100a-d and with a plurality of user devices 1416a-c to communicate with and support the health monitoring applications 1112 residing on the plurality of gateways 1100a-d. The health monitoring server application 1408 may be a web-based application supported by the central application server 1400. For example, the central application server 1400 may be a web server and support the health monitoring server application 1408 via a website. In another embodiment, the health monitoring application 1112 is a stand-alone application that is downloaded to the gateways 1100a-d by the central application server 1400 and is operable on the gateways 1100a-d without access to the central application server 1400 or only needs to accesses the central application server 1400 for additional information, such as biosensor data. Using the health monitoring application 1112, the gateways 1100a-d are configured to track biosensor data 1124 and control certain functions of the gateways 1100a-d and any associated glucose biosensors 100. In addition, the health monitoring server application 1408 supports a user application on one or more user devices 1416a, 1416b, 1416c, as described in more detail with respect to FIG. 15.

The central application server 1400 may also be operable to communicate with a doctor's office, pharmacy or hospital or other caregiver or business 1418 over the communication network 1420 to provide biosensor data and alerts. For example, one or more of the gateways 1100a-d may communicate messages including biosensor data, health alerts, requests for medicine refills or requests for new prescriptions to the health monitoring server application 1408. The health monitoring server application 1408 may then transmit the messages to a doctor's office, pharmacy or hospital or other caregiver or business 1418 over the communication network 1420 as requested or needed.

User Device

Figure 15:
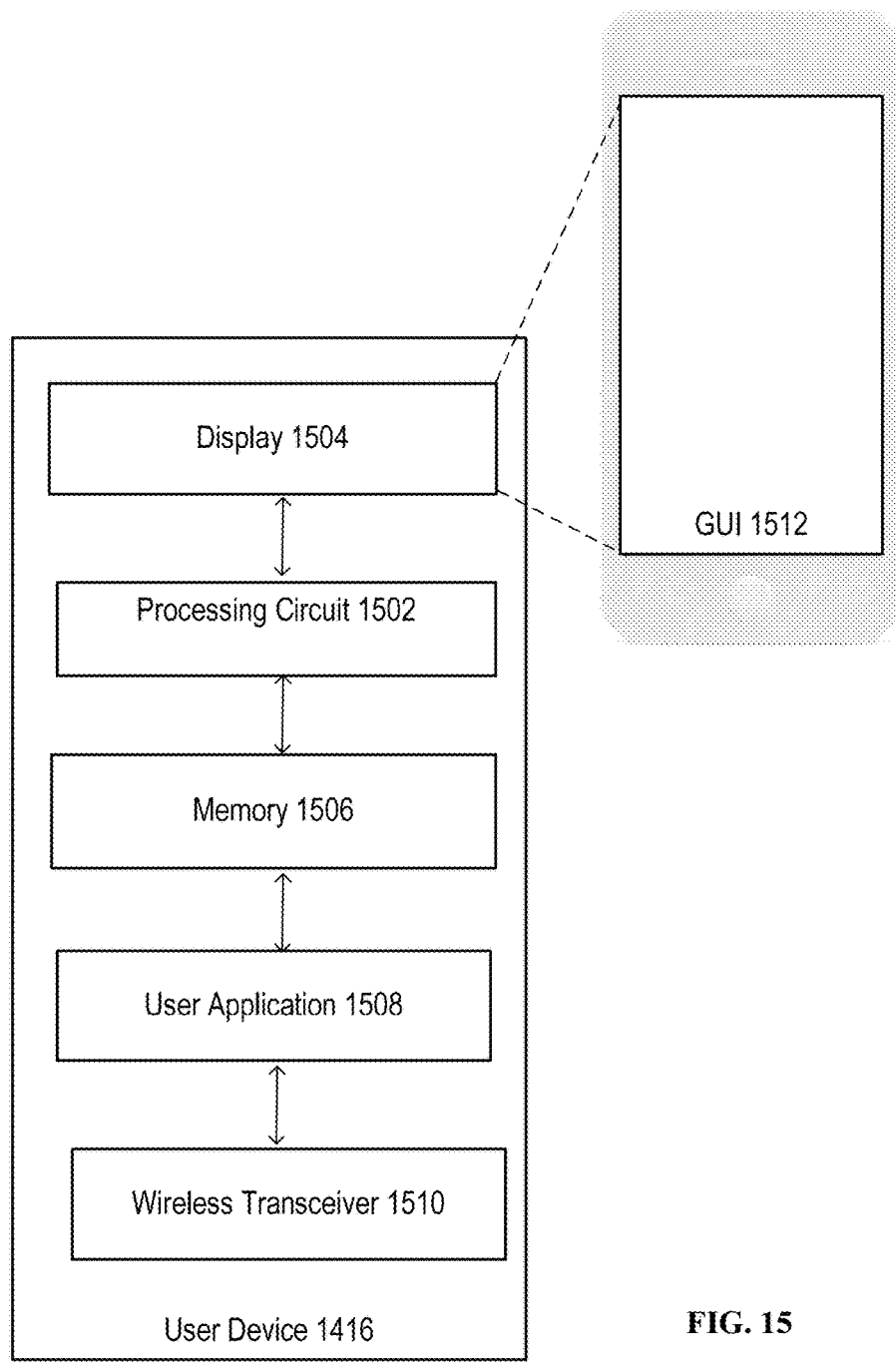
FIG. 15 illustrates a schematic block diagram of an exemplary embodiment of a user device.

FIG. 15 illustrates a schematic block diagram of an embodiment of the user device 1416. The user device 1416 may include a smart phone, laptop, desktop, smart tablet, smart watch, or any other personal user device. In an embodiment, the user device 1416 includes a processing circuit 1502, a display 1504 and a memory 1506. For example, the memory 1506 is a non-transitory processor readable memory that stores instructions which when executed by the processing circuit 1502, causes the processing circuit 1502 to perform one or more functions described herein. The user device 1416 includes a wireless transceiver that is configured to communicate over the communication network 1420 to the central application server 1400 or to one or more gateways 1100.

The user device 1416 further includes a user application 1508. The user application 1508 may be a web-based application supported by the central application server 1400. For example, the central application server 1400 may be a web server and support the user application 1508 via a website. The user device 1416 may then use a web browser or other HTML enabled application to access either all or parts of the user application 1508 via the website supported by the central application server 1400. The user application 1508 is then run within the web browser. In another embodiment, the user application 1508 is a stand-alone application that is downloaded to the user device 1416 and is operable on the user device 1416 without access to the web server or only needs to accesses the web server for additional information, such as biosensor data. In another embodiment, the user application 1508 may be a mobile application designed for download and use by a mobile phone or other mobile device.

The user application 1508 is configured to control certain functions of the glucose biosensor 100. For example, the user application 1508 may generate a GUI 1512 on the display 1504 that includes a graphical selection of commands for controlling the glucose biosensor 100, such as a rest mode command or re-calibrate command. The authorized user may input commands into the user device 1416 to control the operation of the glucose biosensor 100, glucose meter 1200 or other biosensors.

In addition, the user application 1500 is configured to track and display bio sensor data. For example, the user application 1500 receives biosensor data from the central application server 1400 or directly from a glucose biosensor 100 or gateway 1100 and stores the biosensor data. The user application 1500 may then upon request generate a GUI 1512 that includes a graphical display of glucose levels or other biosensor data over a requested period of time, such as one day, one week, etc. The user application 1508 may issue alerts when biosensor data reaches certain predetermined thresholds. For example, when the user device 1416 receives notice of a glucose level measurement from the central application server 1400 or a gateway 1100 that reaches or exceeds a predetermined high or low threshold, the user application 1508 displays and sounds an alert message. In general, a good range for blood sugar levels is between 70 milligrams/deciliter (mg/Dl) and 150 mg/Dl. When the sugar level are lower than 70 mg/Dl or greater than 150 mg/Dl, the alert message may include a request for an alternate glucose monitoring method be performed to confirm the glucose levels, such as a finger prick method. The alert may also trigger warnings to inject insulin or perform other corrective health measures. In addition, the user device 1416 may transmit immediate health alerts when a dangerous level of glucose is detected, such as lower than 40 mg/Dl or over 240 mg/Dl and a message with advice that the patient performs certain corrective measures, such as injection of insulin.

The user application 1508 may also generate a GUI 1512 that allows a user to input data, such as glucose measurements determined by the finger prick method. Such measurements may be communicated back to the glucose biosensor 100 for calibration and to the central application server 1400 for storage.

In another example, the user application 1508 generates a GUI 1512 that allows a user to input when a meal is consumed by the patient. Since glucose targets depend on timing of meals, this information may be used in the tracking and charting of glucose levels. For example, the American Diabetes Association suggests the following targets for most nonpregnant adults with diabetes. More or less stringent glycemic goals may be appropriate for each individual: Before a meal (preprandial plasma glucose): 80-130 mg/dl and 1-2 hours after beginning of the meal (Postprandial plasma glucose): Less than 180 mg/dl.

The user application 1508 may also track activity and generate one or more GUIs 1512 on the display 1504 that includes an activity tracker display. The activity tracker display may include periods of rest or sleep and periods of activity along with biosensor data for such periods, such as pulse, glucose levels, oxygen levels, temperature, blood pressure, etc.

Figure 16:
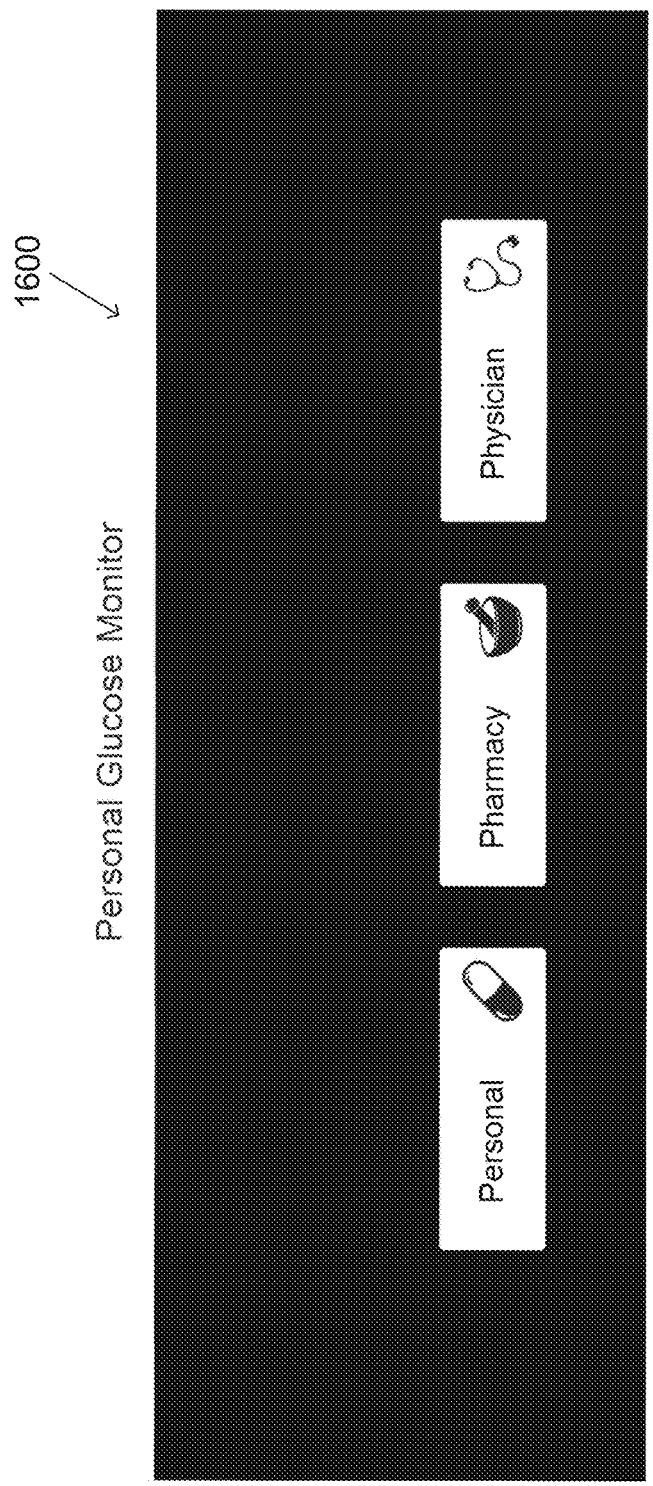
FIG. 16 illustrates a schematic block diagram of an exemplary embodiment of a graphical user interface.

FIG. 16 illustrates a schematic block diagram of an embodiment of a graphical user interface (GUI) 1600 generated by the user application 1508. The user application 1508 may generate the GUI 1600, e.g. on the user device. The GUI 1600 provides an interface for a personal authorized user, pharmacy or physician to login and use the application.

Figure 17:
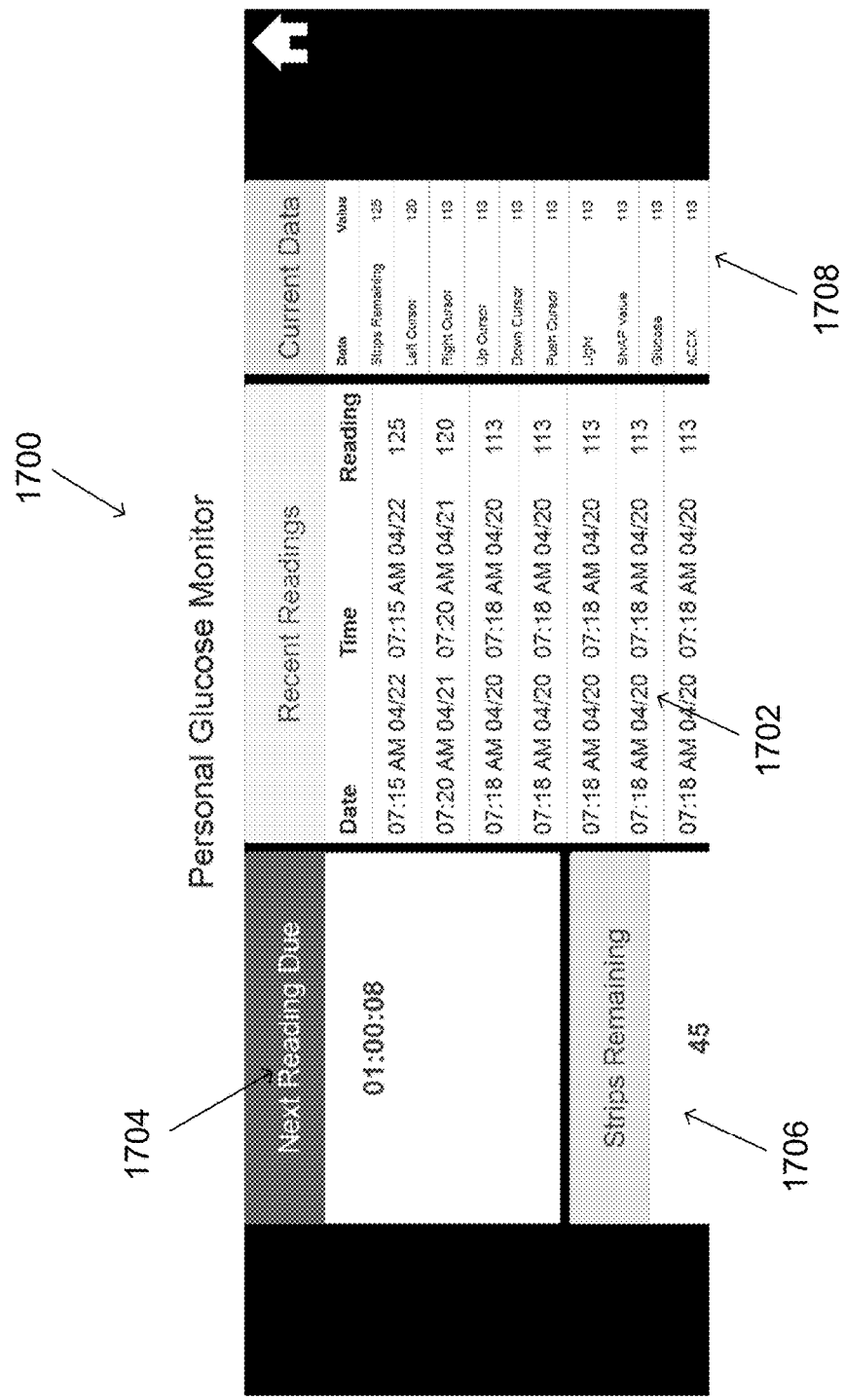
FIG. 17 illustrates a schematic block diagram of an exemplary embodiment of another graphical user interface.

FIG. 17 illustrates a schematic block diagram of another embodiment of a graphical user interface (GUI) 1700 generated by the user application 1508. The user application 1508 may generate the GUI 1700, e.g. on the user device. The GUI 1700 provides an interface for monitoring glucose levels of a patient. The GUI 1700 illustrates a history of readings of glucose level measurements 1702. The history may display one day, multiple days, one week, month, or a specified time frame. The user application 1508 also tracks a recommended time for a next glucose level measurement. The user application 1508 displays the next reading time 1704 in the GUI 1700. The user application 1508 may also display a number of glucose test strips remaining 1706. The number of glucose test strips may be determined using the scale and weight of a test strip medicine bottle or based on a number of glucose level measurements received from the glucose meter 1200. The user application 1508 is also configured to display current data 1708.

Figure 18:
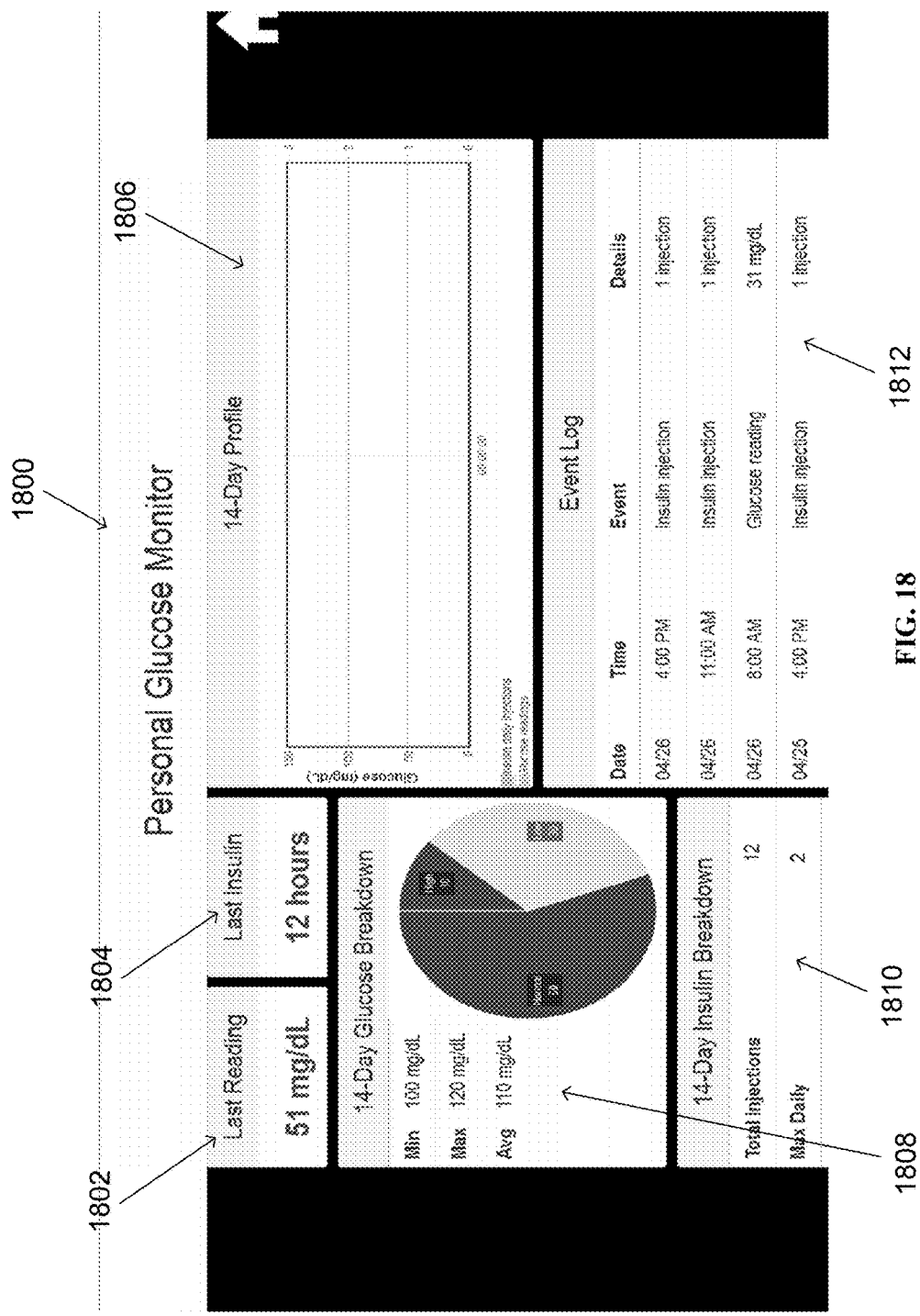
FIG. 18 illustrates a schematic block diagram of an exemplary embodiment of another graphical user interface.

FIG. 18 illustrates a schematic block diagram of another embodiment of a graphical user interface (GUI) 1800 generated by the user application 1508. The user application 1508 may generate the GUI 1800, e.g. on the user device. The GUI 1800 illustrates a history of readings of glucose level measurements and insulin dosages. For example, the GUI 1800 illustrates a last reading of a glucose level measurement 1802 and a time of the last insulin dosage 1804. The GUI 1800 illustrates a graphical representation of glucose levels 1806 over a selected period of time. The GUI may also illustrate a pie chart or other graphical representation of minimum, maximum and average glucose level measurements 1808 over a selected period of time. The GUI 1800 further illustrates a history of insulin dosages 1812 over a selected period of time and an overview of the total number of injections, average number of injections or maximum number of injections over a selected period of time 1810.

The GUI 1800 may indicate whether a glucose level measurement is from the glucose meter 1200 or from the glucose biosensor 100. For example, in an embodiment, the glucose level measurement from the glucose biosensor 100 is used as an indicator, e.g. for tracking and charting glucose levels over a period of time, while readings from the glucose meter 1200 are used for more accurate measurements or verification.

Figure 19:
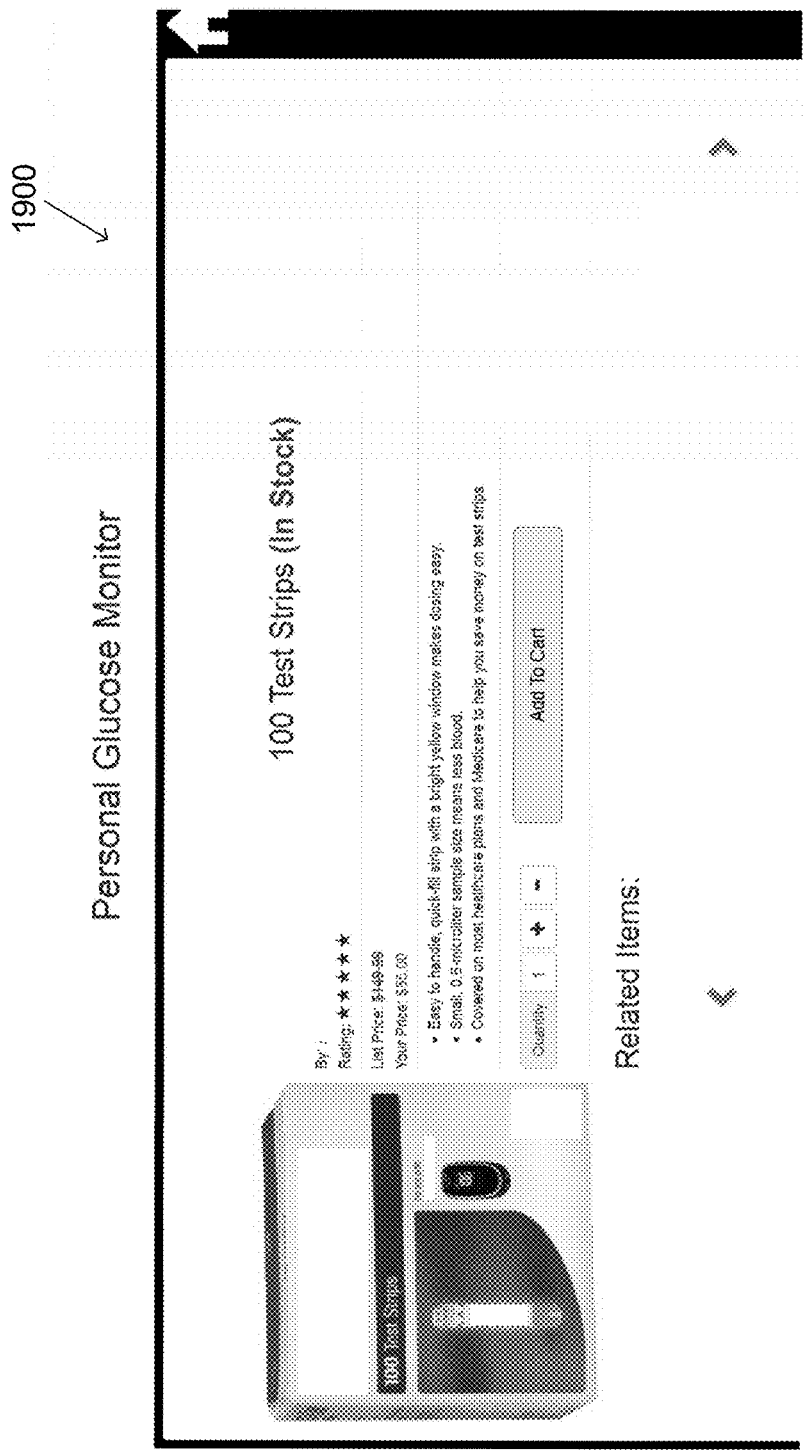
FIG. 19 illustrates a schematic block diagram of an exemplary embodiment of another graphical user interface.

FIG. 19 illustrates a schematic block diagram of another embodiment of a graphical user interface (GUI) 1900 generated by the user application 1508. The user application 1508 may generate the GUI 1900, e.g. on the user device. The GUI 1900 provides an interface for ordering glucose test strips. The user application 1508 may generate a request or alert, and then the GUI 1900 alert when a number of glucose test strips remaining is less than a predetermined threshold. The test strips may then be re-ordered using the GUI 1900.

The glucose monitoring system thus provides reliable, non-invasive optical measurements of glucose levels. This non-invasive method may be used with humans or animals without requiring numerous painful finger pricks throughout a day.

Exemplary Embodiments of the Analytic Biosensor

The above described embodiment of a glucose biosensor 100 still requires calibration using a glucose meter 1200. For example, frequent, even daily calibration with a glucose meter 1200 is sometimes required, and thereby compounds the potential for errors and possible infections. This problem of daily calibration has been difficult to overcome due to various factors including blood emissivity types, tissue color variances, temperature, and even manufactured insulin induced bio-chemical reaction.

In an embodiment, an analytic biosensor is configured to perform monitoring of biometric analytical markers, including glucose levels, using a combination of two or more non-invasive techniques that analyze light reflected from an ear canal. For example, the techniques may include: near infrared spectroscopy, Raman spectroscopy, flourophoresence, thermal emissions, photoacoustic and polarimetry. In use, two or more of the techniques are employed to obtain biometric measurements. An average or mean of the biometric measurements from the two or more techniques are then used for calibration of the analytic biosensor. The analytic biosensor is also configured to non-invasively measure other biometric data, such as pulse rate, blood pressure, peripheral oxygen (SpO2) saturation amounts, body temperature, various electrolytes and many common blood analytic levels, such as bilirubin amount.

Figure 20:
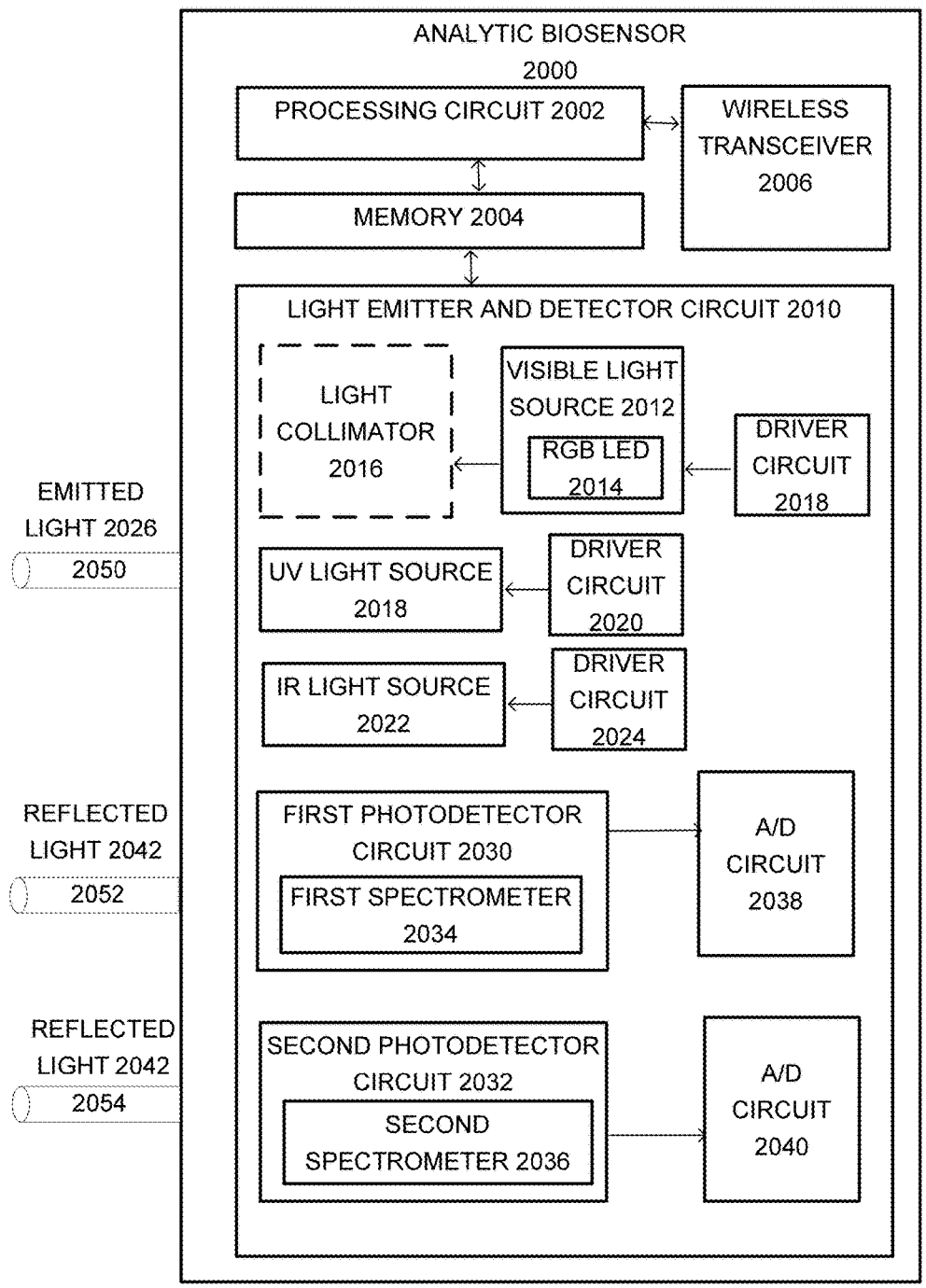
FIG. 20 illustrates a schematic block diagram of an exemplary embodiment of an analytic biosensor.

FIG. 20 illustrates a schematic block diagram of an exemplary embodiment of the analytic biosensor 2000. The analytic biosensor 2000 includes a processing circuit 2002 and a memory 2004. For example, the memory 2004 is a non-transitory processor readable memory that stores instructions which when executed by the processing circuit 2002, causes the processing circuit 2002 to perform one or more functions described herein. The analytic biosensor 2000 includes a wireless transceiver 2006 that is configured to communicate with one or more gateways 1100, similarly as described herein with respect to the glucose biosensor 100. For example, the wireless transceiver 2006 may operate in the 900 MHz range over a serial link using a proprietary protocol or may utilize a standard protocol in the 900 MHz range, such as IEEE 802.11ah, Zigbee, IEEE 802.15-11 etc. In other embodiments, the wireless transceiver 2006 operates in one or more other wireless frequency bands or protocols, such as near field communication, short range radio frequency, RFID, infrared link, Bluetooth, or other short range wireless communication protocol.

The analytic biosensor 2000 also includes a light emitter and detector circuit 2010 having a plurality of light sources. For example, the analytic biosensor 2000 includes a visible light source 2012, a UV light source 2018 and an IR light source 2022. The visible light source 2012 is configured to emit light across a broad spectrum of frequencies and includes, e.g. a tri-color LED, such as an (RGB) LED, wherein each color of the LED is controlled separately. In an embodiment, a driver circuit 2018 is configured to drive each lead or color of the RGB LED separately to generate a broad spectrum of colors to perform various non-invasive measurement techniques, as described further herein. A light collimator 2016, such as a prism, may be used to align a direction of the light emitted from the RGB LED 2014. The analytic biosensor 2000 also includes a UV light source 2018 and an associated driver circuit 2020, and an IR light source 2022 and an associated driver circuit 2024. The plurality of light sources are thus configured to emit frequencies of light across a plurality of classes in the electromagnetic spectrum, including UV, visible and IR light.

The analytic biosensor 2000 includes one or more optical fibers 2050 for transmitting emitted light 2026 from the plurality of light sources into an ear canal. A single optical fiber 2050 may be used for all or some of the plurality of light sources or a different optical fiber may be used for each of the plurality of light sources.

The light emitter and detector circuit 2010 further includes a plurality of photodetector circuits, including at least a first photodetector circuit 2030 and a second photodetector circuit 2032. The first photodetector circuit 2030 and the second photodetector circuit 2032 include, for example, one or more photodiodes, phototransistors or other components operable to detect IF, visible and UV light. The first photodetector circuit 2030 and the second photodetector circuit 2032 may also include a first spectrometer 2034 and a second spectrometer 2036, respectively. The first spectrometer and the second spectrometer detect an intensity of light as a function of wavelength or of frequency. The spectrometers 2034, 2036 are thus each able to perform a spectrum analysis of the reflected light. The first photodetector circuit 2030 and the second photodetector circuit 2032 are coupled to a first A/D circuit 2038 and a second A/D circuit 2040. Alternatively, a single A/D circuit may be coupled to both the first and second photodetector circuits.

The light emitter and detector circuit 102 is optically coupled to a plurality of optical fibers 2052, 2054 for capturing reflected light from the ear canal. In an embodiment, the plurality of optical fibers 2052, 2054 includes at least a first optical fiber 2052 optically coupled to the first photodetector circuit 2030 and a second optical fiber 2054 optically coupled to the second photodetector circuit 2032. Other configurations and numbers of optical fibers may also be employed for capturing the reflected light.

The plurality of optical fibers 2050, 2052 and 2054 are encased within an earpiece or ear bud or other casing that is configured to fit within an outer ear canal of a patient. In an embodiment, the one or more optical fibers 2050 optically coupled to the plurality of light source circuits 2012, 2018, 2022 is configured to rest within the middle of the optical fibers 2052, 2054 coupled to the photodetector circuits, 2030, 2032. However, other configurations and numbers of the plurality of optical fibers 2050, 2052, 2054 may also be implemented.

In use, analytic biosensor 2000 performs a plurality of non-invasive techniques that analyze light reflected from an ear canal. For example, the techniques may include: infrared absorption spectroscopy, Raman spectroscopy, thermal emission spectrometry, flourophoresence, and photoacoustic spectrometry. Various techniques that may be performed by the analytic biosensor 2000 are now described in more detail.

Infrared Absorption Spectroscopy

Infrared absorption spectroscopy is used to provide rapid, non-invasive analysis of a wide range of sample types. This method is based on the principle that every type of molecule has resonance absorption peaks which are directly related to the molecule's concentration in a sample. Thus, reflected radiation from a sample can be analyzed to determine the concentration of glucose and other electrolytes.

In an embodiment, the IR light source 2022 emits a near-IR light that is transmitted by at least one optical fiber 2050 into an ear canal. A plurality of optical fibers 2052, 2054 capture the reflected light and transmit the reflected light 2042 to the first photodetector circuit 2030 and the second photodetector circuit 2032. The first photodetector circuit 2030 and the second photodetector circuit 2032 detect the reflected light and generate an analog signal. The processor analyzes the reflected light to determine the resonance absorption peaks of the reflected light. The determined resonance absorption peaks are compared with the expected resonance absorption peaks for analyte to obtain an analytic concentration measurement. For example, the resonance absorptions peaks are analyzed with the expected resonance absorption peaks for glucose to obtain a glucose level measurement. The expected resonance absorption peaks for pure glucose are determined in the mid infrared ranging from 2.5 µm to about 16 µm along with their magnitudes to be about 75 peaks in the above range with different peak absorption values.

In another embodiment, by comparing the ratio of light absorption from two different frequencies, e.g. 430 nm (Blue Light) and 940 nm (IR Light), a ratio of glucose levels can be calculated based on the Beer-Lambert law. The spectrum of pure glucose can be determined at a wavelength, so the molar attenuation coefficient c at that wavelength can be determined. For example, measurements of decadic attenuation coefficient $\mu_{10}$ are made at one wavelength $\lambda$ (e.g. at approximately 430 nm). This wavelength of 430 nm has been determined as nearly unique for glucose. Next, a second wavelength (e.g. at approximately 940 nm) is then used in order to correct for possible interferences. The concentration c is then given by:

$$c = \frac{\mu_{10}(\lambda)}{\varepsilon(\lambda)}.$$

A glucose level measurement can thus be obtained using infrared absorption spectroscopy.

Raman Spectroscopy

When radiation has an impact upon a sample, most of the incident light suffers Rayleigh scattering and a small portion of light undergoes frequency shifts. The measurement of these frequency shifts is known as Raman spectroscopy. Raman spectroscopy may provide a spectral signature that is less influenced by water than near-infrared absorption spectroscopy.

In an embodiment, the RGB LED 2014 is used as a light source for Raman spectroscopy. The use of three independent controlled drivers enables the RGB LED 2014 to have a broad frequency spectrum. Additionally, the light collimator in front of the RGB LED 2014 may be used to provide a uniform wave front to minimize any dominant peaks across the frequency range of the emitted light 2026.

In an embodiment, the RGB LED 2014 emits a light across a predetermined frequency range that is transmitted by at least one optical fiber 2050 into an ear canal. A plurality of optical fibers 2052, 2054 capture the reflected light and transmit the reflected light 2042 to the first photodetector circuit 2030 and the second photodetector circuit 2032. The first spectrometer and the second spectrometer 2036 each determine a frequency shift in the reflected light from the predetermined frequency range of the emitted light. The processor analyzes the frequency shift of the reflected light 2042 from the emitted light 2026 to obtain an analytic concentration measurement, for example, a glucose level measurement.

Thermal Emission Spectrometry

Thermal emission Spectrometry (TES) is based on the principle that natural mid-infrared emission from the human body, especially the tympanic membrane in the ear canal, is modulated by the state of the emitting tissue. Radiation from the human body possesses information about spectral characteristics of the object and is determined by absolute body temperatures as well as by the properties and states of the emitting body tissue.

One can measure radiation from the skin of the human body or, more reliably, quantify the infrared emission from the tympanic membrane. The tympanic membrane is known to be in an excellent position to measure, for example, body temperature because it shares the blood supply with the hypothalamus, the center of core body temperature regulation. The tympanic thermometer measures the integral intensity of infrared radiation in the ear canal. It is inserted into the ear canal so as to sufficiently enclose the detector apparatus such that multiple reflections of radiation from the tympanic membrane transform the auditory canal into a "black body" cavity, a cavity with emissivity theoretically equal to one. In such a way a sensor can get a clear view of the tympanic membrane and its blood vessels for measuring the amount of infrared radiation emitted by the patient's tympanic membrane. This infrared radiation is spectrally modified by the tissue when compared with the theoretical "black body" radiation as shown in Planck and Kirchhoff's law. Thus infrared radiation has the spectral characteristics of, for example, the blood in the tympanic membrane of the ear canal. This allows measurements of the concentration of blood constituencies by spectral analysis of infrared radiation naturally emitted from the human body.

A sensor inserted in the ear canal can clearly obtain a view of the membrane and its blood vessels to measure the emitted IR radiation. See, e.g., U.S. Pat. No. 5,823,966, entitled, "Non-invasive continuous blood glucose monitoring," issued on Oct. 20, 1998, which is incorporated by reference herein. It describes that a spectral characteristic of various constituencies of the tissue will be separated using non-dispersive correlation spectroscopy methods. It relies on the use of a negative correlation filter placed in front of an infrared detector. The negative correlation filter blocks radiation in the absorption bands for the analyte to be measured at one of the infrared detector windows when the other infrared detector window is covered by another filter capable of blocking radiation in such a way that does not include absorption bands characteristic for the analyte at all wavelengths in the range of interest. Distinguishing the radiation intensity between two detector windows, which is done on the detector level because of the physical construction of the detector, provides a measure proportional to to obtain an analytic concentration measurement, for example, a glucose level measurement.

In an embodiment, naturally reflected IR light from the ear canal of a patient is captured by a plurality of optical fibers 2052, 2054. The reflected IR light includes the infrared radiation naturally emitted by the human body. No light source is used prior to detecting this naturally emitted IR light. The first photodetector circuit 2030 includes an infrared detector with an IF filter sensitive to an IR glucose signature. The second photodetector circuit 2032 measures the intensity of the reflected IR light without such IF filter. The processor then determines a ratio of intensities of the reflected light detected by the first photodetector circuit 2030 and the second photodetector circuit 2032. The ratio provides a measure proportional to the analytic concentration of glucose.

A glucose level measurement can thus be obtained using thermal emission spectroscopy.

Fluorescence

Fluorescence is a property present in certain molecules, called fluorophores, in which they emit a photon shortly after absorbing one with a higher energy wavelength. Fluorescence may be used to measure the concentration of glucose using a fluorophores, such as one or more sensitive proteins that have been found in glucose. The glucose concentration is translated into a power or energy level in the fluorescence.

One particular technique for fluorescence-based non-invasive glucose monitoring is based on the measurement of cell auto-fluorescence due to the compound NAP(P)H and signaling of changes in extracellular glucose concentrations by fluorescent markers of mitochondrial metabolism. In one example, fluorescent emissions in the range of 430 nm have been detected and used to develop correlations to glucose concentrations.

In an embodiment, the visible light source 2012 emits light in the 430 nm range that is transmitted by at least one optical fiber 2050 into an ear canal. A plurality of optical fibers 2052, 2054 capture the reflected light and transmit the reflected light 2042 to the first photodetector circuit 2030 and the second photodetector circuit 2032. The first photodetector circuit 2030 and the second photodetector circuit 2032 detect the reflected light 2042 and determine a power or energy level of the fluorescent emission in the 430 nm range in the reflected light 2042. The processor analyzes the fluorescent emission of the reflected light 2042 and correlates the fluorescent emission to a glucose concentration to obtain a glucose level measurement.

A glucose level measurement can thus be obtained using fluorescence.

Photoacoustic Spectrometry

When incoming light is modulated, the absorbing sample warms and cools in a cycle. If the cycle is fast enough and the sample does not have time to expand and contract in response to the modulated light, a change in pressure develops. This pressure "wave" can lead to production of sound waves. These sounds waves can be detected by a sensitive microphone or piezoelectric elements. Likewise these sound waves can also be detected by optical methods using the deflection of light. Modulation frequencies can vary from single digit to thousands of hertz. The light to sound interaction can be used to determine several blood markers as well as indicators in other areas, such as glucose. The specific generated sound waves may be correlated to specific key blood markers. The ear drum is ideal to receive and transmit acoustic signals for pressure changes. Specific audio tones injected into the ear drum as well as specific optical signals can be monitored to detect blood markers.

In an embodiment, the visible light source 2012 emits light in the 430 nm range that is transmitted by at least one optical fiber 2050 into an ear canal. A plurality of optical fibers 2052, 2054 capture the reflected light and transmit the reflected light 2042 to the first photodetector circuit 2030 and the second photodetector circuit 2032. The first photodetector circuit 2030 and the second photodetector circuit 2032 detect the reflected light 2042 and determine a power or energy level of the fluorescent emission in the 430 nm range in the reflected light 2042. The processor analyzes the fluorescent emission of the reflected light 2042 and correlates the fluorescent emission to a glucose concentration to obtain a glucose level measurement. A glucose level measurement can thus be obtained using photoacoustic spectrometry.

The analytic biosensor 2000 is thus configured to obtain glucose level measurements using a plurality of measurement techniques, including infrared absorption spectroscopy, Raman spectroscopy, thermal emission spectrometry, flourophoresence, and photoacoustic spectrometry. The analytic biosensor 2000 may then wirelessly transfer the glucose level measurement to a gateway or glucose meter or user device. In another embodiment, the analytic biosensor 2000 may include a wired network interface card that is operable to communicate with a user device or gateway over a wired connection. The interface card may include a USB, mini-USB, micro-USB or other type of interface for communicating with the user device or gateway.

In an embodiment, the analytic biosensor 2000 is configured to determine a percentage of blood that is loaded with oxygen using pulse oximetry. The percentage of hemoglobin, the protein in blood that carries oxygen, within the blood SpO2 (Saturation of peripheral oxygen) is measured using the "tympanic" membrane inside the ear canal.

For example, the visible light source 2012 emits light having a first wavelength, e.g. of 660 nm ("red light"), and the IR light source 2022 emits IR light having a second wavelength, e.g. of 940 nm. Absorption of light at these wavelengths differs significantly between blood loaded with oxygen and blood lacking oxygen. Oxygenated hemoglobin absorbs more of the IR light and allows more of the red light to pass through. Deoxygenated hemoglobin allows more of the IR light to pass through and absorbs more of the red light. The visible and IR light sources 2012, 2022 sequence through a cycle of alternating off and on for the two frequencies. Ambient light may also be measured such that the processor may cancel out the foreground noise of the ambient light interface from the measurement. The ratio of the two absorptions (oxygenated hemoglobin versus deoxygenated hemoglobin) is converted to the saturation level of peripheral oxygen SpO2 by the processing circuit 2002 based on the Beer-Lambert law.

Bilirubin concentrations in the blood and other types of analytes for example can be measured by similar techniques as described above. For example, sodium and potassium levels or concentrations may be measured using similar techniques as described above.

Figure 21:
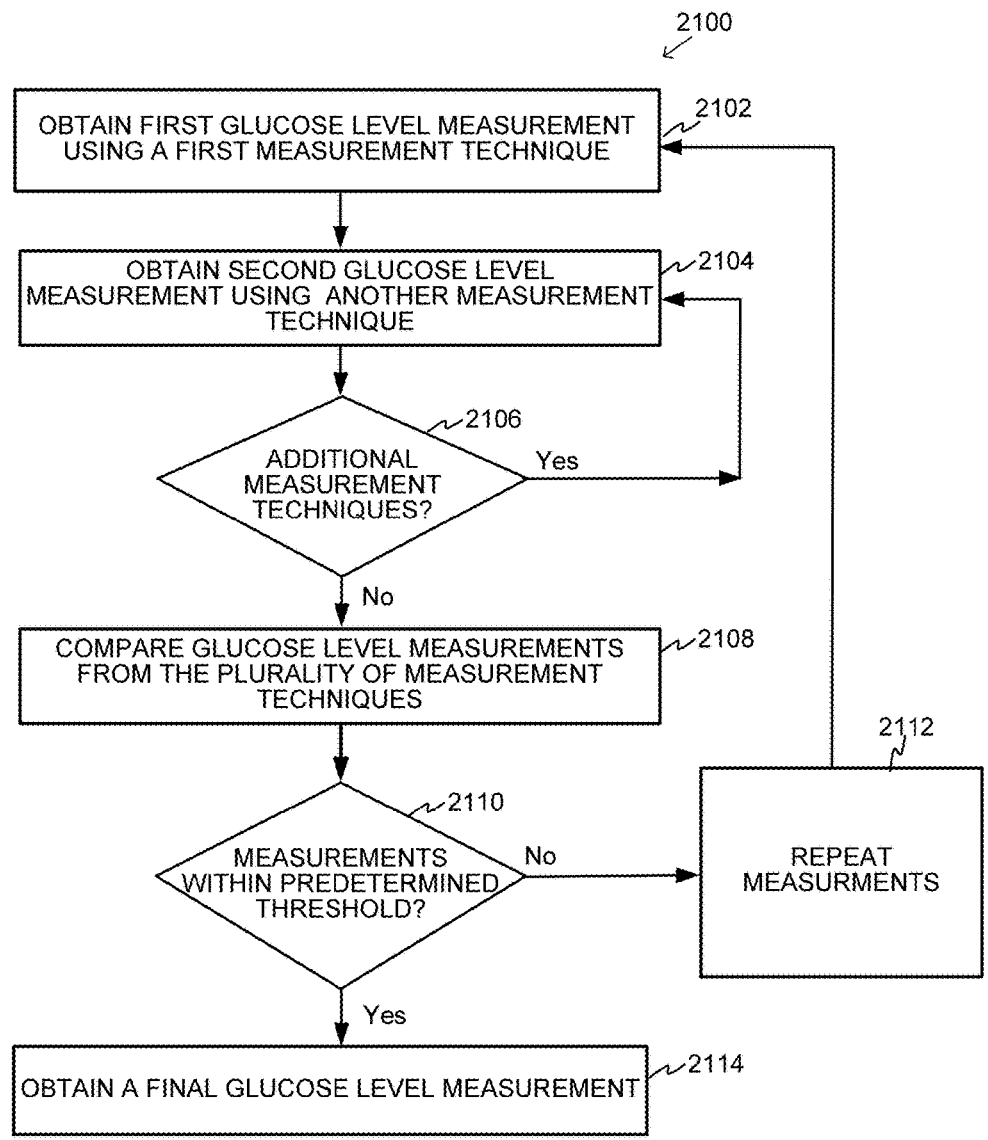
FIG. 21 illustrates a logical flow diagram of an exemplary method for obtaining a glucose level measurement using a plurality of measurement techniques.

FIG. 21 illustrates a logical flow diagram of an exemplary method 2100 for obtaining a glucose level measurement using a plurality of measurement techniques. A glucose level measurement is obtained using a first measurement technique, wherein the first measurement technique includes at least one of: Near-Infrared Spectrometry, Raman spectrometry, Thermal Emission Spectrometry, Fluorescence and Photoacoustic Spectrometry 2102. Another glucose level measurement is obtained using another measurement technique, wherein the another measurement technique includes a different one of: Near-Infrared Spectrometry, Raman Spectrometry, Thermal Emission Spectrometry, Fluorescence and Photoacoustic Spectrometry 2104. It is then determined whether additional measurement techniques are available or scheduled 2106. If so, another glucose level measurement is obtained using another technique, wherein the another measurement technique includes a different one of: Near-Infrared Spectrometry, Raman Spectrometry, Thermal Emission Spectrometry, Fluorescence and Photoacoustic Spectrometry 2104.

If no other measurement techniques are scheduled or available 2106, the glucose level measurements obtained from the plurality of measurement techniques are compared 2108. When the glucose level measurements are determined to be within a predetermined threshold, e.g. within a 10% margin of error threshold 2110, a final glucose measurement is obtained from the plurality of measurement techniques 2114. The final glucose measurement may be obtained by calculating an average or a mean of the glucose level measurements obtained from the plurality of measurement techniques.

When the glucose level measurements are not within a predetermined threshold, e.g. within a 10% margin of error threshold 2110, one or more of the glucose level measurements may be repeated 2112. Bilirubin concentrations in the blood and other types of analytes for example can be measured using a similar method.

Figure 22:
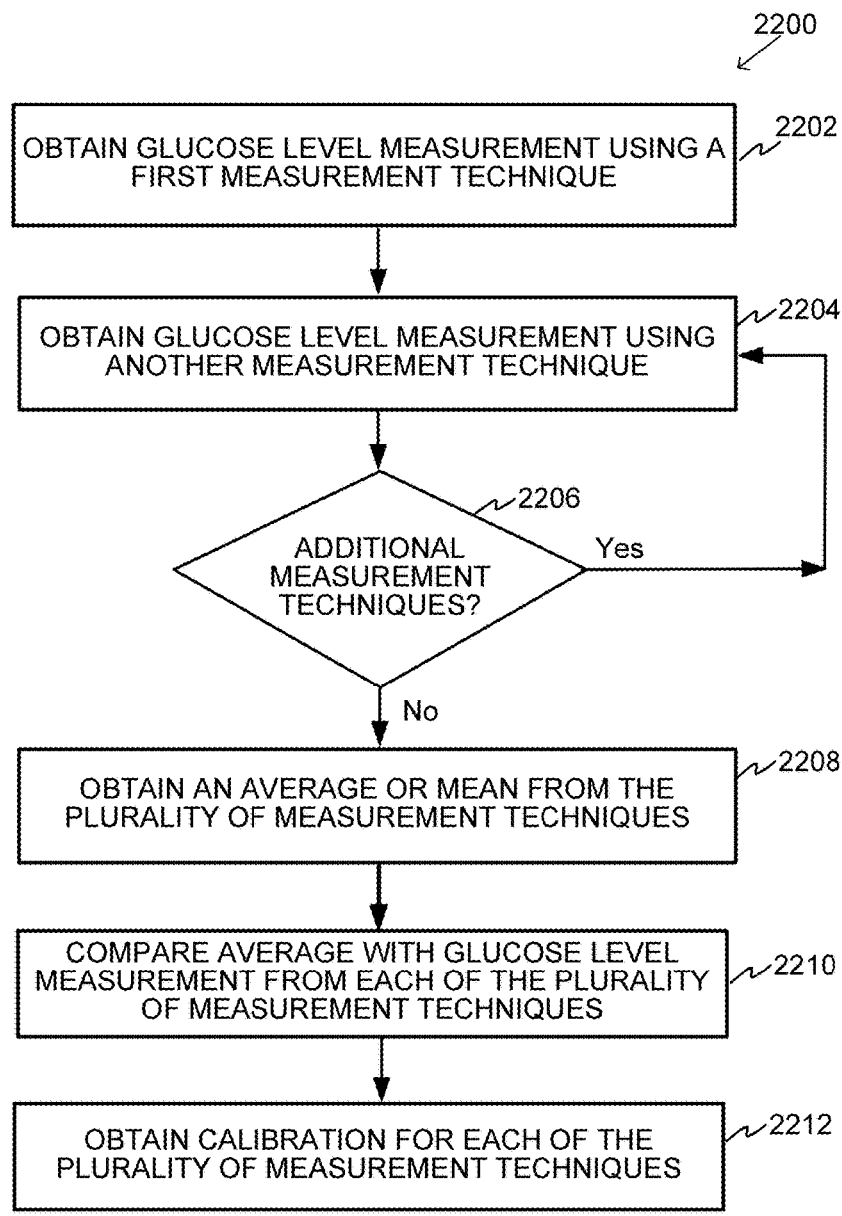
FIG. 22 illustrates a logical flow diagram of an exemplary method for using a combination of measurement techniques to enable auto calibration.

FIG. 22 illustrates a logical flow diagram of an exemplary method 2200 for using a combination of measurement techniques to enable auto calibration. A glucose level measurement is obtained using a first measurement technique, wherein the first measurement technique includes at least one of: Near-Infrared Spectrometry, Raman spectrometry, Thermal Emission Spectrometry, Fluorescence and Photoacoustic Spectrometry 2202. Another glucose level measurement is obtained using another measurement technique, wherein the another measurement technique includes a different one of: Near-Infrared Spectrometry, Raman Spectrometry, Thermal Emission Spectrometry, Fluorescence and Photoacoustic Spectrometry 2204. It is then determined whether additional measurement techniques are available or scheduled 2206. If so, another glucose level measurement is obtained using another technique, wherein the another measurement technique includes a different one of: Near-Infrared Spectrometry, Raman Spectrometry, Thermal Emission Spectrometry, Fluorescence and Photoacoustic Spectrometry 2204.

When no other measurement techniques are scheduled or available 2206, obtain an average or mean of the glucose level measurements obtained from the plurality of measurement techniques 2208. The average or mean is then compared with the individual glucose level measurements from each of the plurality of measurement techniques 2210. For example, a difference between an individual glucose level measurement and the average or mean is determined. Then, a calibration is obtained for each of the plurality of measurement techniques based on the comparison 2212. For example, a difference between an individual glucose level measurement from a first one of the plurality of measurement techniques and the average or mean is determined. When the average or mean has a difference of 2% from the individual glucose level from a first one of the plurality of measurement techniques, then a calibration of 2% is assigned to the first one of the plurality of measurement techniques.

This calibration process may be performed hourly, daily, or weekly as needed. The use of a plurality of calibration techniques thus allows for auto-calibration of the analytic biosensor 2000. Bilirubin concentrations in the blood and other types of analytes for example can be measured using a similar method. For example, sodium and potassium levels or concentrations may be measured as well using a plurality of measurement techniques.

Figure 23:
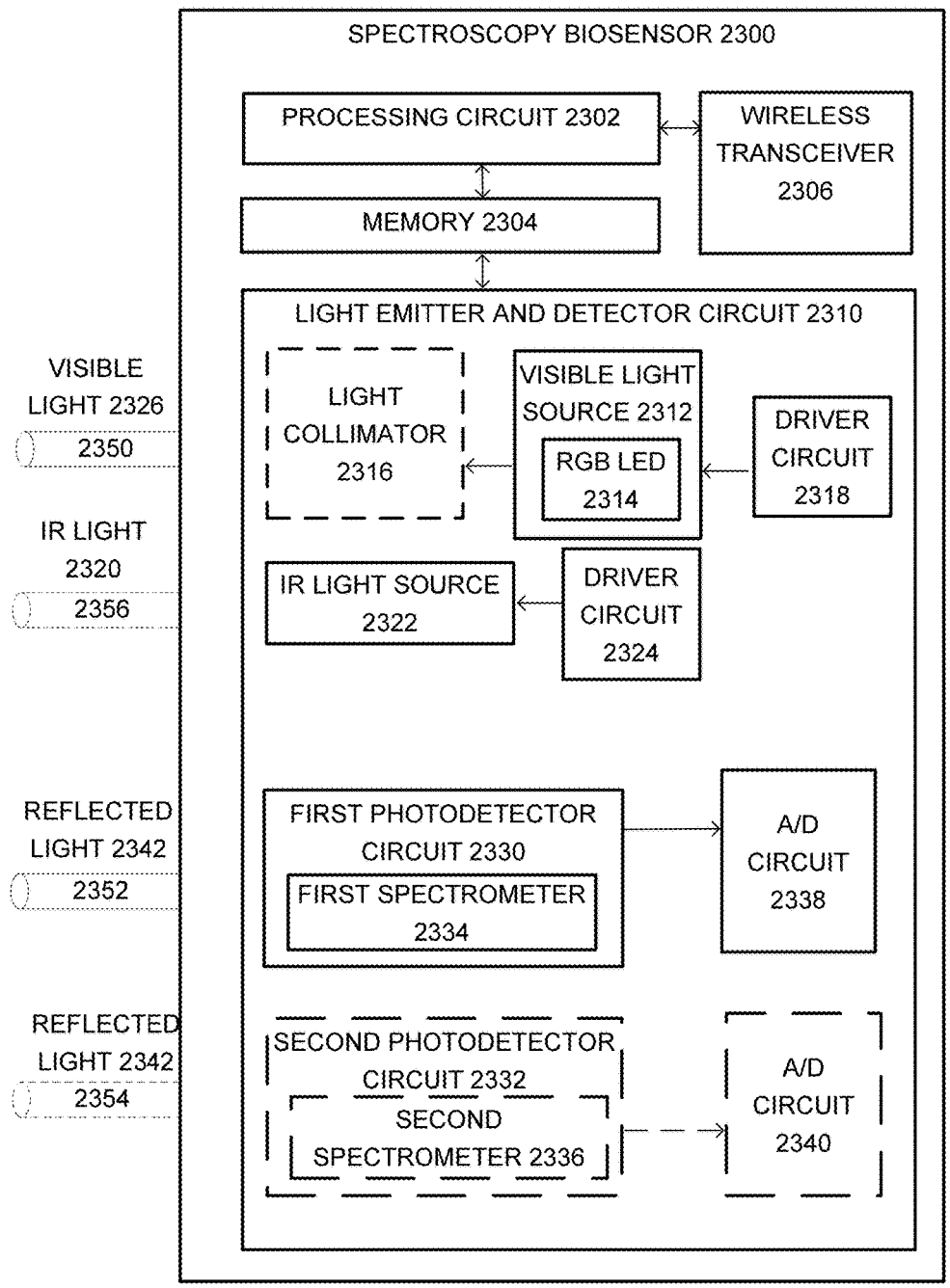
FIG. 23 illustrates a schematic block diagram of an exemplary embodiment of an IR spectroscopy biosensor.

FIG. 23 illustrates a schematic block diagram of an exemplary embodiment of a spectroscopy biosensor 2300. The spectroscopy biosensor 2300 is configured to detect blood analytes, including glucose, using IR absorption spectroscopy. In this embodiment, the spectroscopy biosensor 2300 is configured as an ear biosensor in the one or more form factors described herein. The spectroscopy biosensor 2300 includes a processing circuit 2302 and a memory 2304. For example, the memory 2304 is a non-transitory processor readable memory that stores instructions which when executed by the processing circuit 2302, causes the processing circuit 2302 to perform one or more functions described herein. The spectroscopy biosensor 2300 includes a wireless transceiver 2306 that is configured to communicate directly with a user device 1416 or with one or more gateways 1100, similarly as described herein with respect to the glucose biosensor 100. For example, the wireless transceiver 2306 may operate in the 900 MHz range over a serial link using a proprietary protocol or may utilize a standard protocol in the 900 MHz range, such as IEEE 802.11ah, Zigbee, IEEE 802.15-11 etc. In other embodiments, the wireless transceiver 2306 operates in one or more other wireless frequency bands or protocols, such as near field communication, short range radio frequency, RFID, infrared link, Bluetooth, or other short range wireless communication protocol.

The spectroscopy biosensor 2300 includes a light emitter and detector circuit 2310 having a plurality of light sources for emitting IR light and visible light. For example, the spectroscopy biosensor 2300 includes a visible light source 2312 and an IR light source 2322. The visible light source 2312 is configured to emit light across a broad spectrum of frequencies and includes, e.g. a laser or tri-color LED, such as an (RGB) LED, wherein each color of the LED is controlled separately. In an embodiment, a driver circuit 2318 is configured to drive each lead or color of the RGB LED separately to generate a broad spectrum of colors to perform various non-invasive measurement techniques, as described further herein. A light collimator 2316, such as a prism, may be used to align a direction of the light emitted from the RGB LED 2314. The spectroscopy biosensor 2300 also includes an IR light source 2322 and an associated driver circuit 2324. The spectroscopy biosensor 2300 is thus configured to emit frequencies of light in at least the visible and IR electromagnetic spectrum.

The spectroscopy biosensor 2300 includes one or more optical fibers 2350, 2356 for transmitting emitted light from the plurality of light sources into an ear canal. A first optical fiber 2350 may be used to transmit visible light 2326 emitted from the visible light source 2312 into the ear canal and a second optical fiber 2356 may be used to transmit IR light emitted from the IR light source 2322 into the ear canal. In another embodiment, a single optical fiber may transmit both the visible light 2326 and the IR light 2320 into the ear canal.

The light emitter and detector circuit 2310 further includes one or more photodetector circuits, e.g., a first photodetector circuit 2330 and a second photodetector circuit 2332. The first photodetector circuit 2330 and the second photodetector circuit 2332 include, for example, one or more photodiodes, phototransistors or other components operable to detect IR and visible light. The first photodetector circuit 2330 and the second photodetector circuit 2332 may also include a first spectrometer 2334 and a second spectrometer 2336, respectively or may share a single spectrometer. The first photodetector circuit 2330 and the second photodetector circuit 2332 may be separate components are included in a single component. The first spectrometer 2334 and the second spectrometer 2336 detect an intensity of light as a function of wavelength or of frequency. The spectrometers 2334, 2336 are thus each able to perform a spectrum analysis of the reflected light. The first photodetector circuit 2330 and the second photodetector circuit 2332 are coupled to a first A/D circuit 2338 and a second A/D circuit 2340. Alternatively, a single A/D circuit may be coupled to both the first and second photodetector circuits 2330, 2332.

The light emitter and detector circuit 2310 is optically coupled to one or more optical fibers 2352, 2354 for capturing reflected light 2342 from the ear canal. In an embodiment, the optical fibers 2352, 2354 includes at least a first optical fiber 2352 optically coupled to the first photodetector circuit 2330 and a second optical fiber 2354 optically coupled to the second photodetector circuit 2332. In another embodiment, only one photodetector circuit is employed wherein a single optical fiber 2352 is employed for capturing reflected IR and visible light and coupled to the single photodetector circuit 2330 for detecting the reflected IR and visible light. In another embodiment, an optical fiber is not employed but an earbud with an aperture is used to capture reflected light. Other configurations and numbers of optical fibers or other component or methods may also be employed for capturing the reflected light.

The plurality of optical fibers 2350, 2352, 2354, 2356 may be encased within an earpiece or ear bud or other casing that is configured to fit within an outer ear canal of a patient. In an embodiment, the one or more optical fibers 2350, 2356 optically coupled to the plurality of light source circuits 2312, 2322 are configured to rest within the middle of the optical fibers 2352, 2354 coupled to the photodetector circuits, 2330, 2332. However, other configurations and numbers of optical fibers may also be implemented.

In use, the spectroscopy biosensor 2300 performs infrared absorption spectroscopy to detect blood analytes and in specific to detect glucose. In an embodiment, the IR light source 2322 emits an IR light that is transmitted by at least one optical fiber 2356 into the ear canal. A plurality of optical fibers 2352, 2354 capture the reflected IR light and transmit the reflected IR light 2342 to the first photodetector circuit 2330 and the second photodetector circuit 2332. The first photodetector circuit 2330 and the second photodetector circuit 2332 detect the reflected IR light. The first and second spectrometers 2334, 2336 each analyze the reflected IR light to determine a first frequency or wavelength response and a second frequency or wavelength response of the resonance absorption peaks of the reflected IR light. The first and second frequency/wavelength responses may be summed, averaged or otherwise processed to obtain a final frequency/wavelength response of the resonance absorption peaks of the reflected IR light.

The visible light source 2312 then emits a visible light that is transmitted by at least one optical fiber 2350 into the ear canal. The plurality of optical fibers 2352, 2354 capture the reflected visible light and transmit the reflected visible light 2342 to the first photodetector circuit 2330 and the second photodetector circuit 2332. The first photodetector circuit 2330 and the second photodetector circuit 2332 detect the reflected visible light. The first and second spectrometers 2334, 2336 each analyze the reflected visible light to determine a spectrum response such as, the resonance absorption peaks of the reflected visible light. The spectrum response includes spectral lines that illustrate an intensity or power or energy at a frequency or wavelength in a spectral region of the reflected light. The first spectral response generated by the first spectrometer 2334 and the second spectral response generated by the second spectrometer 2336 may be summed, averaged or otherwise processed to obtain a final spectral response of the resonance absorption peaks of the reflected visible light.

The ratio of the resonance absorption peaks from the visible and IR light can be calculated based on the Beer-Lambert law to determine a glucose level. The spectral response of pure glucose is determined, so the molar attenuation coefficient ε can be determined. For example, the resonance absorption peaks for pure glucose in the mid infrared ranging from 2.5 µm to about 16 µm along with their magnitudes are about 75 peaks in the above range with different peak absorption values.

Measurements of decadic attenuation coefficient $\mu_{10}$ are made at the IF light wavelength λ and at a second wavelength for the visible light in order to correct for possible interferences. The concentration c may then be determined from the Beer-Lambert Law as:

$$c = \frac{\mu_{10}(\lambda)}{\varepsilon(\lambda)}.$$

In an embodiment, the wavelength of the IR light is in the IR range from approximately 700 nanometers (frequency 430 THz) to approximately 1 mm (300 GHz). More specifically, the IR light may have a wavelength of approximately 940 nm. In an embodiment, the wavelength of the visible light is in the visible light range from approximately 390 nm to 700 nm (430-770 THz). More specifically, the visible light may be blue light having a wavelength in the range of 420-495 nm. In specific, the visible light may have a wavelength of approximately 430 nm. It has been determined that the resonance absorption peaks is unique for glucose at this wavelength of 430 nm. The spectroscopy biosensor 2300 thus obtains a glucose level measurement using infrared absorption spectroscopy.

For example, it is possible to measure the difference in absorption spectra of glucose and water at a first wavelength $\lambda_1$ and the absorption of water at a second wavelength $\lambda_2$. According to the Beer-Lambert law, light intensity will decrease logarithmically with path length l (such as through an artery of length l). Assuming then an initial intensity $I_{in}$ of light is passed through a path length l, a concentration $C_g$ of glucose may be determined using the following equations:

At the first wavelength $\lambda 1, I_1 = I_{in1} * 10^{-(\alpha_{g1} C_{gw} + \alpha_{w1} C_w) * l}$ At the second wavelength $\lambda 2, I_2 = I_{in2} * 10^{-(\alpha_{g2} C_{gw} + \alpha_{w2} C_w) * l}$ wherein:
$I_{in1}$ is the intensity of the initial light at $\lambda_1$
$I_{in2}$ is the intensity of the initial light at $\lambda_2$
$\alpha_{g1}$ is the absorption coefficient of glucose in water at $\lambda_1$
$\alpha_{g2}$ is the absorption coefficient of glucose in water at $\lambda_2$
$\alpha_{w1}$ is the absorption coefficient of water at $\lambda_1$ $\alpha_{w2}$ is the absorption coefficient of water at $\lambda_2$
$C_{gw}$ is the concentration of glucose and water
$C_w$ is the concentration of water
Then letting R equal:

$$R = \frac{\log 10\left(\frac{I1}{Iin1}\right)}{\log 10\left(\frac{I2}{Iin2}\right)}$$

The concentration of glucose Cg may then be equal to:

$$Cg = \frac{Cgw}{Cgw + Cw} = \frac{\alpha_{w2}R - \alpha_{w1}}{(\alpha_{w2} - \alpha_{gw2}) * R - (\alpha_{w1} - \alpha_{gw1})}$$

The IR spectroscopy biosensor 2300 may thus determine the concentration of glucose Cg using spectroscopy at two different wavelengths, a first wavelength in the IR range and a second wavelength in the visible light range. In an embodiment, the first wavelength is approximately 940 nm and the second wavelength is approximately 430 nm. It has been determined that the IR light at 940 nm is highly absorbed by water while the visible light at 430 nm is absorbed as much by glucose.

The IR spectroscopy biosensor 2300 may also function as a pulse oximeter using similar principles under Beer-lambert law to determine pulse and oxygen levels. For example, the first wavelength is approximately 940 nm and the second wavelength is approximately 640 nm when determining pulse and oxygen levels. The IR spectroscopy biosensor 2300 may also detect other types of analytes, such as sodium and potassium, using IR absorption spectroscopy.

Figure 24A:
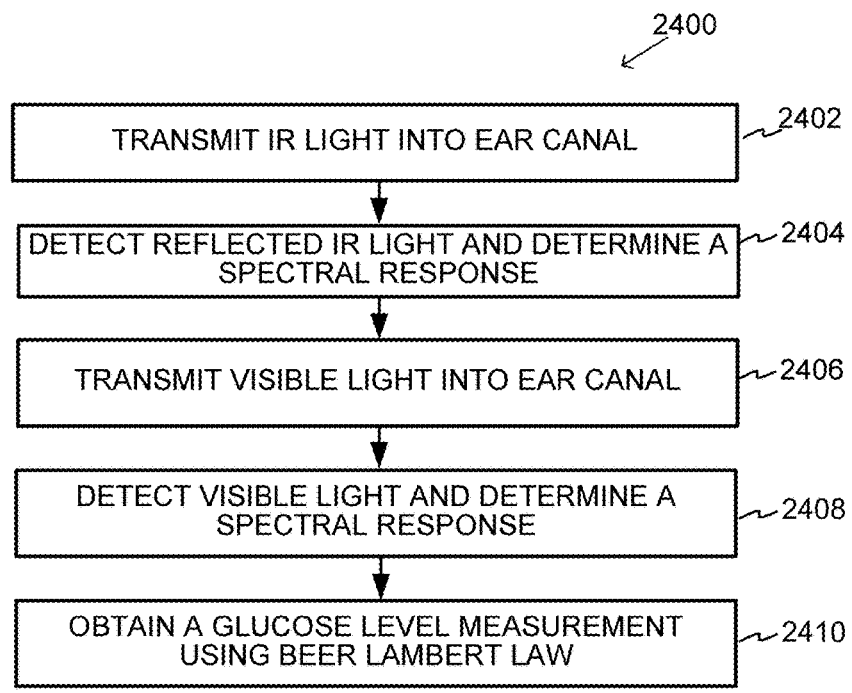
FIG. 24A illustrates a logical flow diagram of an embodiment of a method for glucose monitoring using IR absorption spectroscopy.

FIG. 24A illustrates a logical flow diagram of an embodiment of a method 2400 for glucose monitoring using absorption spectroscopy. An IR light is transmitted into the ear canal 2402. The reflected IR light is captured by one or more optical fibers 2352, 2354, and transmitted to one or more of the first photodetector circuit 2330 and the second photodetector circuit 2332. The reflected IR light is detected and a spectral response is determined 2404. For example, when two photodetectors are utilized, the first and second spectrometers 2334, 2336 perform a spectrum analysis to determine a first spectral response and a second spectral response. The first and second spectral responses may be summed, averaged or otherwise processed to obtain a final frequency/wavelength response of the reflected IR light.

A visible light is transmitted into the ear canal 2406. The reflected visible light is captured by one or more optical fibers 2352, 2354 and transmitted to the first photodetector circuit 2330 and the second photodetector circuit 2332. The reflected visible light is detected and a spectral response is determined 2408. For example, when two photodetectors are utilized, the first photodetector circuit 2330 and the second photodetector circuit 2332 detect the reflected visible light. The first and second spectrometers 2334, 2336 each analyze the reflected visible light to determine a first spectral response and a second spectral response of the reflected visible light. The first and second spectral responses may be summed, averaged or otherwise processed to obtain a final frequency response of the reflected visible light.

A glucose level measurement is then obtained using the Beer Lambert Law 2410. For example, the ratio of the resonance absorption peaks from the spectral responses of the visible and IR light can be calculated based on the Beer-Lambert law as described herein or using other methods. In an embodiment, the first IR light has a wavelength of approximately 940 nm and the second visible light has a wavelength of approximately 430 nm. It has been determined that the IR light at 940 nm is highly absorbed by water while the visible light at 430 nm is absorbed less by glucose.

Figure 24B:
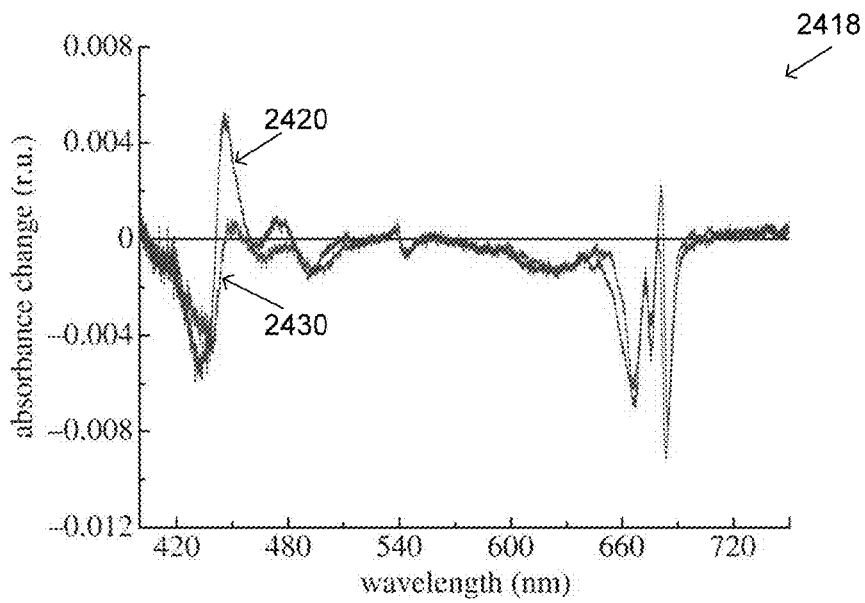
FIG. 24B illustrates a graph of absorbance change versus wavelength for glucose and water.

FIG. 24B illustrates a graph 2418 of absorbance change versus wavelength for glucose and water. The line 2420 illustrates the absorbance change of water while line 2430 illustrates the absorbance change of glucose. As seen in the graph 2418, the absorbance change of water 2420 is greater in the wavelength range between approximately 420 and 450 nm. More specifically, the absorbance change of water 2420 is greater at approximately 430 nm than for glucose 2430. Thus, there are advantages for using a wavelength in the range between approximately 420 and 450 nm, and more specifically at approximately 430 nm.

Since the IR absorption spectroscopy described herein uses two frequencies in different electromagnetic spectrums, e.g. visible and IR light, the glucose level measurements are self-calibrating. The spectroscopy biosensor 2300 thus does not need calibration using another measurement technique, such as the finger prick method. The absorption spectroscopy described herein is thus an accurate, non-invasive blood analytic and glucose monitoring method and device that eliminates the pain of drawing blood as well as eliminates a source of potential infection.

Bilirubin concentrations in the blood and other types of analytes for example may also be measured by the spectroscopy biosensor 2300 using a similar method based on the Beer-Lambert Law. For example, sodium and potassium levels or concentrations may be measured as well using at least two of UV light, visible light or IR light.

Figure 25:
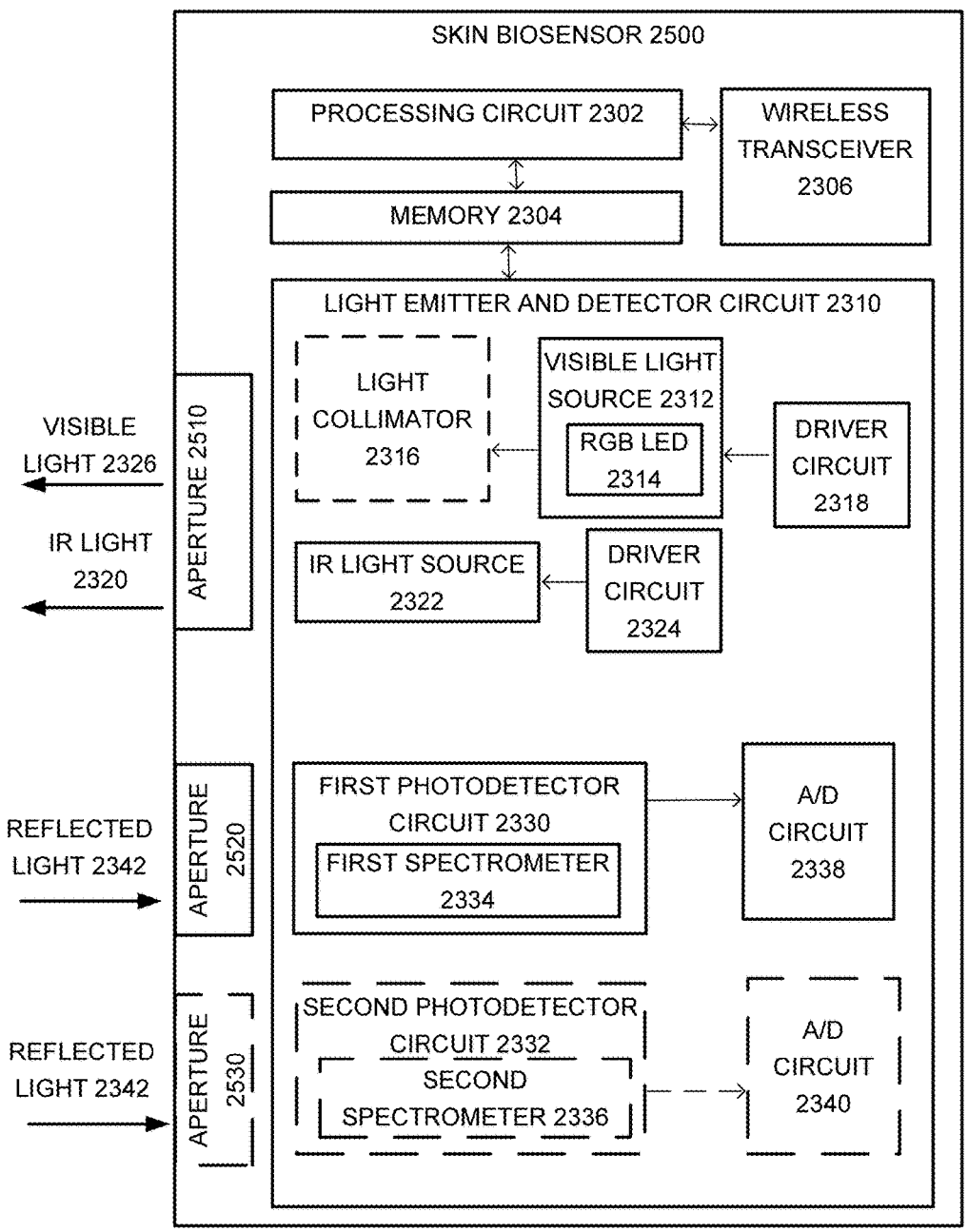
FIG. 25 illustrates a schematic block diagram of an embodiment of a skin biosensor.

FIG. 25 illustrates a schematic block diagram of an embodiment of a skin biosensor 2500. The skin biosensor 2500 includes similar components to the spectroscopy biosensor 2300 and performs absorption spectroscopy to obtain a glucose level measurement. However, instead of measuring glucose levels through the ear canal, the skin biosensor 2500 performs absorption spectroscopy on an area of skin. The area of skin may be located on a fingertip, forehead, behind the ear, arm or other areas of skin. The skin biosensor 2500 may be placed onto the skin area or above the skin area.

The skin biosensor 2500 includes a plurality of apertures for emitting light and collecting light, e.g. rather than the plurality of optical fibers. A first aperture 2510 is positioned with respect to the visible light source 2312 such that visible light 2326 may be emitted onto the skin area. The first aperture 2510 may also be positioned with respect to the IR light source 2322 such that the IR light 2320 may be emitted into the skin area. In another embodiment, two different apertures may be used.

The skin biosensor 2500 further includes a second aperture 2520 positioned to allow reflected light 2342 to be detected by a first photodetector circuit 2330. Optionally, a third aperture 2530 may be used and positioned to allow reflected light 2342 to be detected by a second photodetector circuit 2332. When a second photodetector circuit 2332 is employed, in an embodiment, the first aperture 2510 is located between the second aperture 2520 and the third aperture 2530.

The skin biosensor 2500 performs absorption spectroscopy to obtain a glucose level measurement similarly as described herein using visible light and IR light. The skin biosensor 2500 may also function as a pulse oximeter and/or detect other types of analytes, such as sodium and potassium, using absorption spectroscopy or other measurement techniques described herein. The analytic biosensor 2000 may then wirelessly transfer the glucose level measurement to a gateway 1100 or glucose meter 1200 or user device 1416. In another embodiment, the skin biosensor 2500 may include a wired network interface card that is operable to communicate with a user device 1416 or gateway 1100 over a wired connection. The interface card may include a USB, mini-USB, micro-USB or other type of interface for communicating with the user device or gateway.

Figure 26:
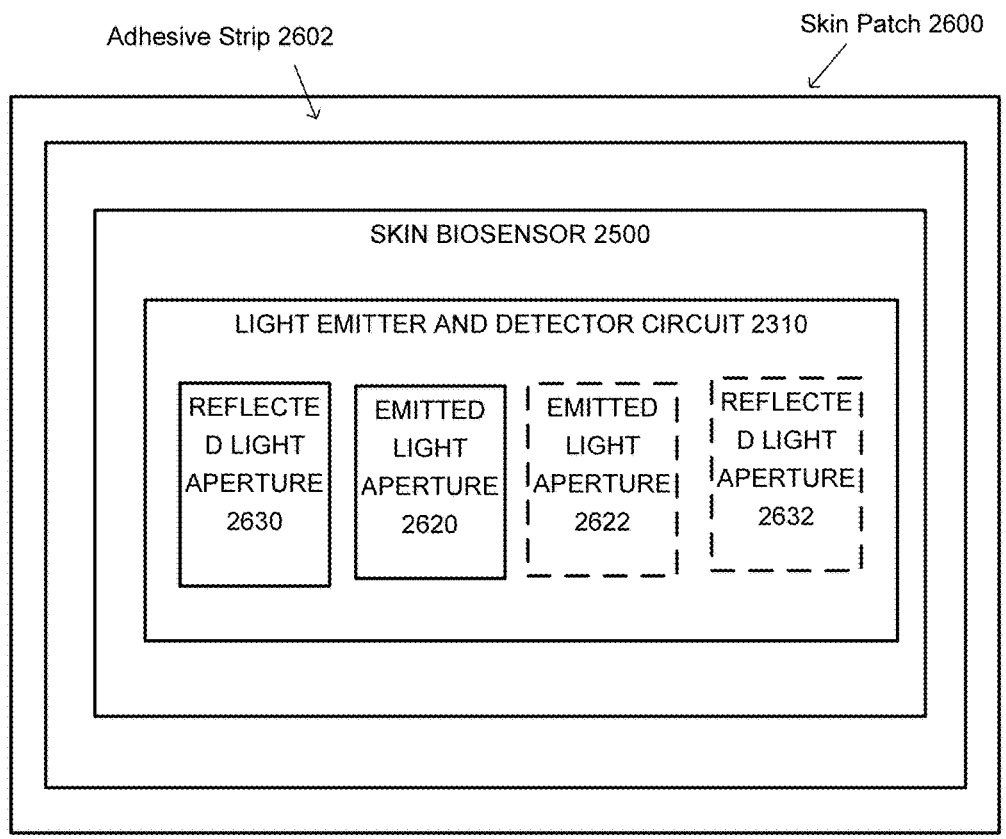
FIG. 26 illustrates a schematic block diagram of an embodiment of a skin patch including a skin biosensor.

FIG. 26 illustrates a schematic block diagram of an embodiment of a skin patch 2600 including a skin biosensor 2500. The skin patch 2600 may include an adhesive strip 2602 to adhere to a skin area. The area of skin may be located on a fingertip, forehead, behind the ear, arm or other areas of skin. The skin biosensor 2500 includes at least one emitted light aperture 2620 positioned to emit IR light and visible light from an IR light source 2332 and visible light source 2312 respectively, as shown in FIG. 25. In another embodiment, the at least one emitted light aperture 2620 is positioned to emit IR light from the IR light source 2332 while a second emitted light aperture 2622 is positioned to emit visible light from the visible light source 2312. Other numbers and configurations of emitted light apertures 2620, 2622 may be also employed. In an embodiment, the one or more emitted light apertures 2620, 2622 are positioned between a first reflected light aperture 2630 and a second reflected light aperture 2632. The positioning of the reflected light apertures provides advantages in capturing reflected light from different angles and/or parts of the skin area. In another embodiment, a single reflected light aperture 2630 is used. The skin biosensor 2500 may also function as a pulse oximeter and/or detect other types of analytes using absorption spectroscopy or other measurement techniques.

Figure 27:
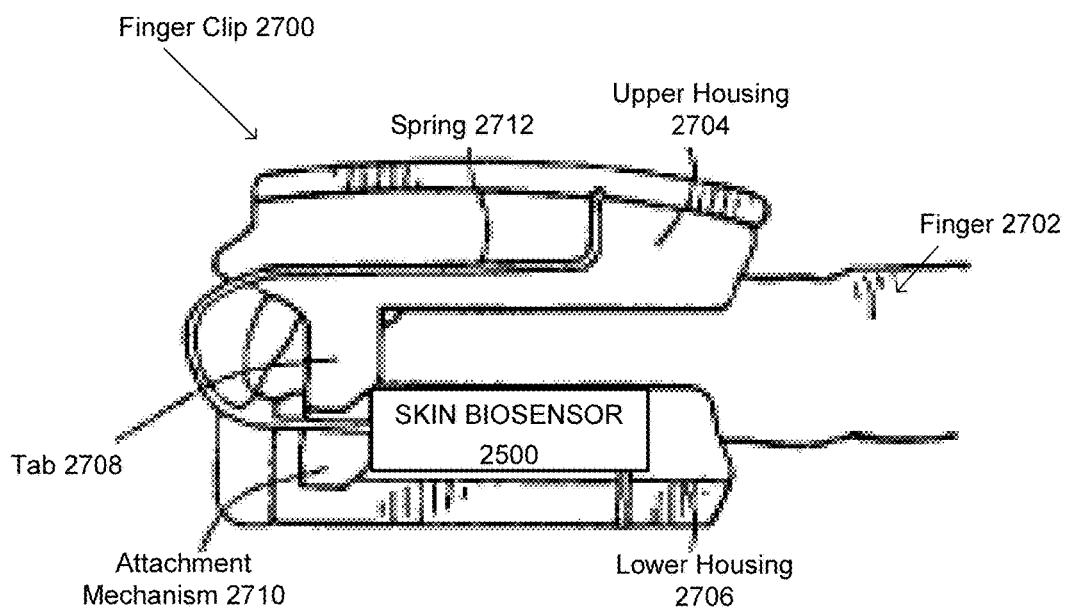
FIG. 27 illustrates a schematic block diagram of an embodiment of a finger clip including the skin biosensor.

FIG. 27 illustrates a schematic block diagram of an embodiment of a finger clip 2700 including the skin biosensor 2500. The finger clip 2700 includes an upper housing 2704 pivoted with respect to a lower housing 2706. The upper housing 2704 and lower housing 2706 are configured to insert a finger 2702. The upper housing 2704 includes a tab 2708 that attaches to the attachment mechanism 2710 of the lower housing 2706. A spring 2712 provides a force to hold the upper and lower housings around the finger 2702.

The skin biosensor 2500 detects a glucose level from an area of skin on the finger 2702, preferably on the fingertip area, using absorption spectroscopy. The skin biosensor 2500 may also function as a pulse oximeter and/or detect other types of analytes using absorption spectroscopy or other measurement techniques described herein.

In another embodiment, the visible light source 2312 and IR light source 2322 are located in the lower housing 2706 of the finger clip 2700 while the one or more photodetector circuits 2330, 2332 are located in the upper housing 2704 of the finger clip 2700. The visible light source 2312 and IR light source 2322 emit light from the lower housing 2706 that is transmitted through a fingertip and detected by the one or more photodetector circuits 2330, 2332 in the upper housing 2704. In other embodiments, the components are reversed, and the visible light source 2312 and IR light source 2322 are located in the upper housing 2704 of the finger clip 2700 while the one or more photodetector circuits 2330, 2332 are located in the lower housing 2706 of the finger clip 2700. The visible light source 2312 and IR light source 2322 emit light from the upper housing 2704 that is transmitted through a fingertip and detected by the one or more photodetector circuits 2330, 2332 in the lower housing 2706.

Figure 28:
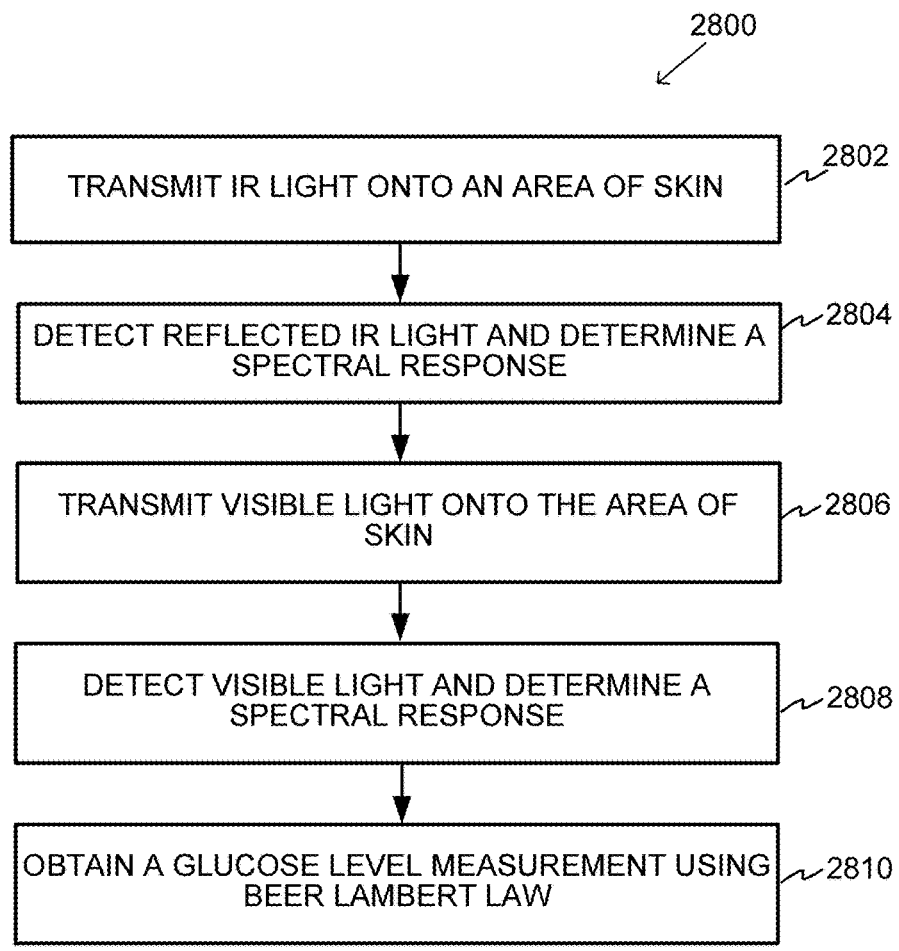
FIG. 28 illustrates a logical flow diagram of an embodiment of another method for glucose monitoring using IR absorption spectroscopy.

FIG. 28 illustrates a logical flow diagram of an embodiment of another method 2800 for glucose monitoring using absorption spectroscopy. An IR light is transmitted onto an area of skin 2802. The reflected IR light is captured by one or more apertures 2520, 2530 and transmitted to one or more photodetectors, 2330, 2332. The reflected IR light is detected and a spectral response is determined 2804. For example, when two photodetector circuits 2330, 2332 are employed, the first and second spectrometers 2334, 2336 perform a spectral analysis to determine intensity levels over spectra of the reflected IR light. The first and second spectral responses may be summed, averaged or otherwise processed to obtain a final spectral response of the reflected IR light.

A visible light is transmitted onto the same area of skin 2806. The reflected visible light is captured by one or more apertures 2520, 2530, and transmitted to one or more photodetectors, 2330, 2332. The reflected visible light is detected and a spectral response is determined 2808. For example, when two photodetector circuits 2330, 2332 are employed, the first photodetector circuit 2330 and the second photodetector circuit 2332 detect the reflected visible light. The first and second spectrometers 2334, 2336 each analyze the reflected visible light to determine a first spectral response and a second spectral response of the reflected visible light. The first and second spectral responses may be summed, averaged or otherwise processed to obtain a final spectral response of the reflected visible light.

A glucose level measurement is then obtained using the Beer Lambert Law 2810 as described herein or using other methods. The measurements may be repeated for a predetermined interval. Thereafter, a rest period may be entered until the next measurements. Bilirubin concentrations in the blood and other types of analytes may also be measured using similar methods based on the Beer-Lambert law as described herein. For example, sodium and potassium levels or concentrations may be measured as well using at least two of UV light, visible light or IR light.

Various embodiments of non-invasive glucose monitoring are described herein. The embodiments help to provide an accurate, non-invasive blood analytic and glucose monitoring methods and devices. The embodiments may be self-calibrating or need only occasional calibration by other techniques. This eliminates the need for the finger prick method to check glucose levels thus reducing the pain of drawing blood as well as eliminating a source of potential infection.

A processing circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

What is claimed is:

1. A biosensor, comprising:
    a first visible light source configured to emit visible light into an ear canal;
    a second infrared (IR) light source configured to emit IR light into the ear canal;
    a plurality of optical fibers encased within an earpiece configured to fit within an outer ear canal and each configured for capturing the reflected IR light and the reflected visible light from the ear canal;
    a first photodetector configured to detect the reflected IR light and the reflected visible light captured by a first one of the plurality of optical fibers and determine a first spectral response of the reflected IR light and a first spectral response of the reflected visible light; and
    a second photodetector configured to detect the reflected IR light and the reflected visible light captured by a second one of the plurality of optical fibers and determine a second spectral response of the reflected IR light and a second spectral response of the reflected visible light;
    a processing circuit configured to obtain a glucose level measurement using the first and second spectral responses of the reflected visible light detected by the first photodetector and the second photodetector respectively and the first and second spectral responses of the reflected IR light detected by the first photodetector and the second photodetector respectively; and
    a wireless transceiver configured to transmit the glucose level measurement.

2. The biosensor of claim 1, wherein the biosensor further comprises:
   at least one optical fiber optically coupled to the first visible light source and the second IR light source, wherein the at least one optical fiber is centrally located between the plurality of optical fibers encased within an earpiece configured for capturing the reflected IR light and the reflected visible light from the ear canal.

3. The biosensor of claim 1, wherein the processing circuit is further configured to obtain a final spectral response of the reflected IR light using a combination of the first spectral response of the reflected IR light detected by the first photodetector and the second spectral response of the reflected IR light detected by the second photodetector.

4. The biosensor of claim 3, wherein the processing circuit is further configured to obtain a final spectral response of the reflected visible light using a combination of the first spectral response of the reflected visible light detected by the first photodetector and the second spectral response of the reflected visible light detected by the second photodetector.

5. The biosensor of claim 1, wherein the first and the second photodetector are configured to detect the reflected IR light and the reflected visible light from surrounding tissue of at least one of: the inner canal or the outer ear canal.

6. The biosensor of claim 5, wherein the processing circuit is further configured to determine the glucose level measurement based on the first and second spectral responses of both the reflected visible light and the reflected IR light by:
   obtaining a final spectral response of the reflected visible light using the first and second spectral responses of the reflected light;
   obtaining a final spectral response of the reflected IR light using the first and second spectral responses of the IR light;
   determining a ratio of light absorption from the final spectral response of the reflected visible light to the final spectral response of the reflected IR light; and
   obtaining the glucose level measurement using Beer-Lambert calculations and the ratio of light absorption.

7. The biosensor of claim 6, wherein the visible light has a wavelength in a range of approximately 390 nm to 450 nm.

8. The biosensor of claim 7, wherein the visible light has a wavelength of approximately 430 nm.

9. The biosensor of claim 6, wherein the IR light has a wavelength in a range of approximately 700 nm to 1 mm.

10. The biosensor of claim 9, wherein the IR light has a wavelength of approximately 940 nm.

11. A biosensor, comprising:
   a first visible light source configured to emit visible light on an area of skin;
   a second infrared (IR) light source configured to emit IR light on the area of skin;
   at least one photodetector configured to detect a spectral response of the visible light reflected from the area of the skin and a spectral response of the IR light reflected from the area of skin;
   a processing circuit configured to:
      determine a ratio of light absorption by the area of the skin using the spectral response of the visible light to the spectral response of the IR light;
      obtain a glucose level measurement using the ratio of light absorption by the area of the skin determined using the spectral response of the visible light to the spectral response of the IR light; and
   a wireless transceiver configured to transmit the glucose level measurement.

12. The biosensor of claim 11, wherein the at least one photodetector includes:
   at least one spectrometer to determine a spectral response of the reflected IR light and a spectral response of the reflected visible light.

13. The biosensor of claim 11, wherein the processing circuit is further configured to obtain the glucose level measurement using the ratio of light absorption and Beer-Lambert calculations.

14. The biosensor of claim 11, wherein the biosensor further comprises a plurality of photodetectors, and wherein the plurality of photodetectors comprise:
   a first photodetector configured to receive the reflected IR light captured by a first one of a plurality of optical fibers and determine a first spectral response of the reflected IR light; and
   a second photodetector configured to receive the reflected IR light captured by a second one of the plurality of optical fibers and determine a second spectral response of the reflected IR light; and
   wherein the processing circuit is further configured to obtain a final spectral response of the reflected IR light based on the first spectral response of the reflected IR light and the second spectral response of the reflected IR light.

15. The biosensor of claim 11, wherein the biosensor further comprises a plurality of photodetectors, and wherein the plurality of photodetectors comprise:
   a first photodetector configured to receive the reflected visible light captured by a first one of a plurality of optical fibers and determine a first spectral response of the reflected visible light; and
   a second photodetector configured to receive the reflected visible light captured by a second one of the plurality of optical fibers and determine a second spectral response of the reflected visible light; and
   wherein the processing circuit is further configured obtain a final spectral response of the reflected visible light based on the first spectral response of the reflected visible light and the second spectral response of the reflected visible light.

16. The biosensor of claim 11, wherein the visible light has a wavelength of approximately 430 nm and wherein the IR light has a wavelength of approximately 940 mm.

17. A biosensor, comprising:
   a first visible light source configured in a finger attachment to emit visible light into a fingertip;
   a second infrared (IR) light source configured in the finger attachment to emit IR light into the fingertip;
   a first photodetector configured in the finger attachment to detect the reflected IR light from the fingertip and the reflected visible light from the fingertip and determine a first spectral response of the reflected IR light and a first spectral response of the reflected visible light; and
   a second photodetector configured in the finger attachment to detect the reflected IR light from the fingertip and the reflected visible light from the fingertip and determine a second spectral response of the reflected IR light and a second spectral response of the reflected visible light;
   a processing circuit configured to obtain a glucose level measurement using the first and second spectral responses of the reflected visible light detected by the first photodetector and the second photodetector respectively and the first and second spectral responses of the reflected IR light detected by the first photodetector and the second photodetector respectively; and a wireless transceiver configured to transmit the glucose level measurement.

18. The biosensor of claim 17, wherein the first and the second photodetector each includes:
   at least one spectrometer configured to detect the reflected IR light and the reflected visible light.

19. The biosensor of claim 18, wherein the processing circuit is further configured to determine the glucose level measurement based on the first and second spectral responses of both the reflected visible light and the reflected IR light by:
   obtaining a final spectral response of the reflected visible light using the first and second spectral responses of the reflected light;
   obtaining a final spectral response of the reflected IR light using the first and second spectral responses of the IR light;
   determining a ratio of light absorption from the final spectral response of the reflected visible light to the final spectral response of the reflected IR light; and
   obtaining the glucose level measurement using Beer-Lambert calculations and the ratio of light absorption.

20. The biosensor of claim 17, wherein the visible light has a wavelength of approximately 430 nm and wherein the IR light has a wavelength of approximately 940 nm.

* * * * *